(12) United States Patent
    Alon

(10) Patent No.: US 11,129,716 B2
(45) Date of Patent: *Sep. 28, 2021

(54) CARDIAC VALVE REPLACEMENT

(71) Applicant: Cardiac Implants LLC, Tarrytown, NY (US)

(72) Inventor: David Alon, Zichron Yaacov (IL)

(73) Assignee: Cardiac Implants, LLC, Tarrytown, NY (US)

( * ) Notice: Subject to any disclaimer, the term of this patent is extended or adjusted under 35 U.S.C. 154(b) by 127 days.

This patent is subject to a terminal disclaimer.

(21) Appl. No.: 16/158,575

(22) Filed: Oct. 12, 2018

(65) Prior Publication Data

US 2019/0038411 A1    Feb. 7, 2019

Related U.S. Application Data

(63) Continuation of application No. 14/364,060, filed as application No. PCT/IB2012/057138 on Dec. 10, 2012, now Pat. No. 10,143,553.

(Continued)

(51) Int. Cl.
    *A61F 2/24* (2006.01)
    *A61B 17/068* (2006.01)
    (Continued)

(52) U.S. Cl.
    CPC .......... *A61F 2/2466* (2013.01); *A61B 17/068* (2013.01); *A61F 2/2409* (2013.01);
    (Continued)

(58) Field of Classification Search
    CPC ..... A61B 2/2427; A61B 2/243; A61B 2/2433; A61B 2/2466; A61F 2/2409;
    (Continued)

(56) References Cited

U.S. PATENT DOCUMENTS

| 688,592 | A | 12/1901 | Chadwick |
|---|---|---|---|
| 4,042,979 | A | 8/1977 | Angell |

(Continued)

FOREIGN PATENT DOCUMENTS

| CN | 1684644 A | 10/2005 |
|---|---|---|
| CN | 2782049 | 5/2006 |

(Continued)

OTHER PUBLICATIONS

Cohn, et al., "The Evolution of Mitral Valve Surgery," Am heart Hosp. J. 2003:1 pp. 40-46 (2003).

(Continued)

*Primary Examiner* — Elizabeth Houston
*Assistant Examiner* — Lindsey Bachman
(74) *Attorney, Agent, or Firm* — Potomac Law Group, PLLC

(57) ABSTRACT

A heart valve annulus repair device having a tissue engaging member and a plurality of anchors. The tissue engaging member includes a loop of wire. Each of the anchors has a pointy front end and a back end and a slot that runs in a front-to-back direction. The anchors are distributed about the loop of wire with the front ends of the plurality of anchors facing the heart valve annulus and with the loop of wire passing through the slots. The device further includes means for implanting the anchors into the heart valve annulus tissue so that the tissue engaging member becomes affixed to the heart valve annulus.

15 Claims, 34 Drawing Sheets

Related U.S. Application Data

(60) Provisional application No. 61/569,304, filed on Dec. 12, 2011, provisional application No. 61/683,736, filed on Aug. 16, 2012.

(51) Int. Cl.

| | |
|---|---|
| A61B 17/04 | (2006.01) |
| A61B 17/115 | (2006.01) |
| A61B 17/00 | (2006.01) |
| A61B 17/064 | (2006.01) |
| A61B 17/22 | (2006.01) |

(52) U.S. Cl.
CPC .......... *A61F 2/2418* (2013.01); *A61F 2/2445* (2013.01); *A61B 17/1155* (2013.01); *A61B 2017/00243* (2013.01); *A61B 2017/00557* (2013.01); *A61B 2017/00783* (2013.01); *A61B 2017/0403* (2013.01); *A61B 2017/0409* (2013.01); *A61B 2017/0414* (2013.01); *A61B 2017/0427* (2013.01); *A61B 2017/0438* (2013.01); *A61B 2017/0464* (2013.01); *A61B 2017/0647* (2013.01); *A61B 2017/22068* (2013.01); *A61F 2/2448* (2013.01); *F04C 2270/0421* (2013.01)

(58) Field of Classification Search
CPC ........ A61F 2/2418; A61F 2/2427–2466; A61F 2/2487; A61F 2002/249
See application file for complete search history.

(56) References Cited

U.S. PATENT DOCUMENTS

| | | | |
|---|---|---|---|
| 5,860,951 | A | 1/1999 | Eggers et al. |
| 6,283,961 | B1 | 9/2001 | Underwood et al. |
| 6,306,163 | B1 | 10/2001 | Fitz |
| 6,575,971 | B2 | 6/2003 | Hauck et al. |
| 6,626,930 | B1 | 9/2003 | Allen et al. |
| 6,656,221 | B2 | 12/2003 | Taylor et al. |
| 6,716,243 | B1 | 4/2004 | Colvin et al. |
| 6,718,985 | B2 | 4/2004 | Hlavka et al. |
| 6,723,038 | B1 | 4/2004 | Schroeder et al. |
| 7,314,485 | B2 | 1/2008 | Mathis |
| 7,588,582 | B2 | 9/2009 | Starksen et al. |
| 8,430,926 | B2 | 4/2013 | Kirson |
| 2002/0095175 | A1 | 7/2002 | Brock et al. |
| 2004/0073302 | A1 | 4/2004 | Rourke et al. |
| 2004/0102839 | A1 | 5/2004 | Cohn et al. |
| 2004/0102840 | A1 | 5/2004 | Solem et al. |
| 2004/0220610 | A1 | 11/2004 | Kreidler et al. |
| 2004/0243227 | A1 | 12/2004 | Starksen et al. |
| 2005/0070924 | A1 | 3/2005 | Schaller et al. |
| 2005/0107812 | A1 | 5/2005 | Starksen et al. |
| 2005/0119523 | A1 | 6/2005 | Starksen et al. |
| 2005/0216078 | A1 | 9/2005 | Starksen et al. |
| 2005/0273138 | A1 | 12/2005 | To et al. |
| 2006/0025750 | A1 | 2/2006 | Starksen et al. |
| 2006/0025784 | A1 | 2/2006 | Starksen et al. |
| 2006/0025787 | A1 | 2/2006 | Morales et al. |
| 2006/0058817 | A1 | 3/2006 | Starksen et al. |
| 2006/0069429 | A1* | 3/2006 | Spence .............. A61B 17/0482 623/2.11 |
| 2006/0129188 | A1 | 6/2006 | Starksen et al. |
| 2007/0016286 | A1 | 1/2007 | Herrmann et al. |
| 2007/0016287 | A1 | 1/2007 | Cartledge et al. |
| 2007/0244554 | A1 | 10/2007 | Rafiee et al. |
| 2008/0051823 | A1 | 2/2008 | Makower et al. |
| 2008/0177380 | A1 | 7/2008 | Starksen et al. |
| 2008/0177382 | A1 | 7/2008 | Hyde et al. |
| 2008/0243150 | A1 | 10/2008 | Starksen et al. |
| 2008/0262609 | A1 | 10/2008 | Gross et al. |
| 2009/0076597 | A1 | 3/2009 | Dahlgren et al. |
| 2009/0093890 | A1 | 4/2009 | Gelbart |
| 2009/0177277 | A1 | 7/2009 | Milo |
| 2009/0287304 | A1 | 11/2009 | Dahlgren et al. |
| 2010/0076549 | A1* | 3/2010 | Keidar ................ A61F 2/2445 623/2.36 |
| 2010/0249920 | A1* | 9/2010 | Bolling ................ A61F 2/2466 623/2.11 |
| 2010/0262232 | A1 | 10/2010 | Annest |
| 2011/0106247 | A1 | 5/2011 | Miller et al. |
| 2011/0230961 | A1 | 9/2011 | Langer et al. |
| 2011/0257728 | A1* | 10/2011 | Kuehn ................ A61F 2/2466 623/1.18 |
| 2011/0301701 | A1 | 12/2011 | Padala et al. |
| 2012/0010700 | A1 | 1/2012 | Spenser |
| 2013/0331930 | A1 | 12/2013 | Rowe et al. |
| 2014/0309730 | A1 | 10/2014 | Alon et al. |
| 2016/0120645 | A1 | 5/2016 | Alon |

FOREIGN PATENT DOCUMENTS

| | | |
|---|---|---|
| CN | 102215784 A | 10/2011 |
| JP | 2007514455 A | 6/2007 |
| JP | 2009507532 A | 2/2009 |
| JP | 2010511469 A | 4/2010 |
| WO | 2005025644 A2 | 3/2005 |
| WO | 2006052687 A1 | 5/2006 |
| WO | 2008068756 A2 | 6/2008 |
| WO | 2009120764 A2 | 10/2009 |
| WO | 2010091383 A2 | 8/2010 |
| WO | 2010108079 A1 | 9/2010 |
| WO | 2012084714 A2 | 6/2012 |
| WO | 2013088327 A1 | 6/2013 |

OTHER PUBLICATIONS

Daimon, et al., "Percutaneous Mitral Valve Repair for Chronic Ischemic Mitral Regurgitation." Journal of the American Heart Association, publ. Apr. 25, 2005.
Desimone, et al., "Adjustable Tricuspid Valve Annuloplasty Assisted by Intraoperative Transesophageal." The American Journal of Cardiology vol. 71 pp. 926-931 Apr. 15, 1993.
Felger, M.D., et al., "Robot-assisted Sutureless Minimally Invasive Mitral Valve Repair", Cardiovascular Surgery, Surgical Technology International XII, p. 185-187 (undated).
Folliguet, et al., "Mitral valve repair robotic versus stemotomy" European Journal of Cardio-Thoracic Surgery 29 (2006) pp. 362-366.
Greelish et al., "Minimally invasive mitral valve repair suggests earlier operations for mitral valve," The Journal of thoracic & Cardiovascular Surgery vol. 126, No. 2 (2003).
International Search Report and Written Opinion for application No. PCT/US2016/014397 dated May 9, 2016.
International Search Report and Written Opinion for International Application No. PCT/IB2014/000949 dated Jan. 20, 2015.
International Search Report and Written Opinion in corresponding application PCT/IB2012/057138, 14 pages, dated Feb. 28, 2013.
Maniu, MD, et al. :Acute & Chronic Reduction of Functional Mitral Regurgitation Journal of Merican College of Cardiology, vol. 44, No. 8, pp. 1652-1661 (2004).
Notice of Allowance dated Oct. 16, 2018 (Heisei 30) in counterpart Japanese application No. JP 2016-517696 citing JP 2009-507532.
Office Action for Japanese Patent Application No. 2014-545447 dated Oct. 31, 2016 (includes English language translation).
Office Action for U.S. Appl. No. 14/364,060 dated Nov. 23, 2016.
Office Action dated Aug. 18, 2017, in Chinese Patent Application 201610004737.X.
Office Action issued in Japanese application No. JP 2016-517696 dated Feb. 19, 2018.

* cited by examiner

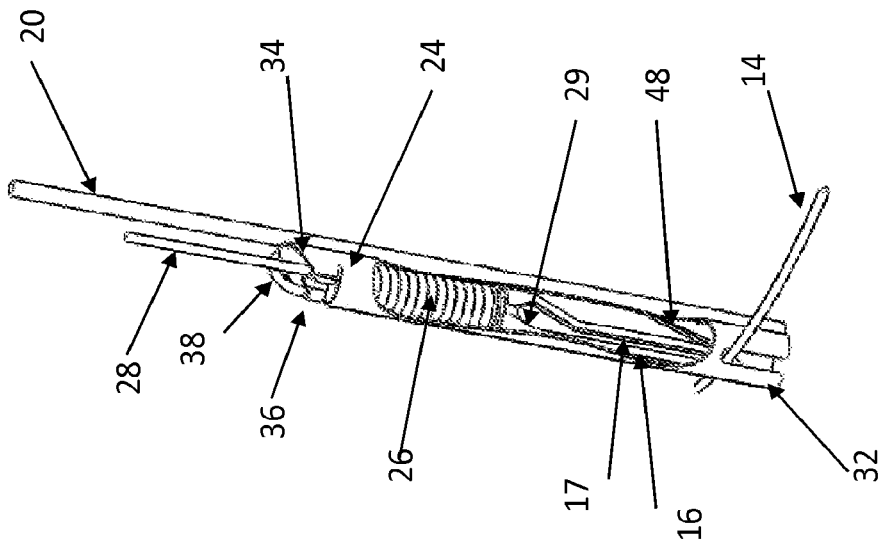
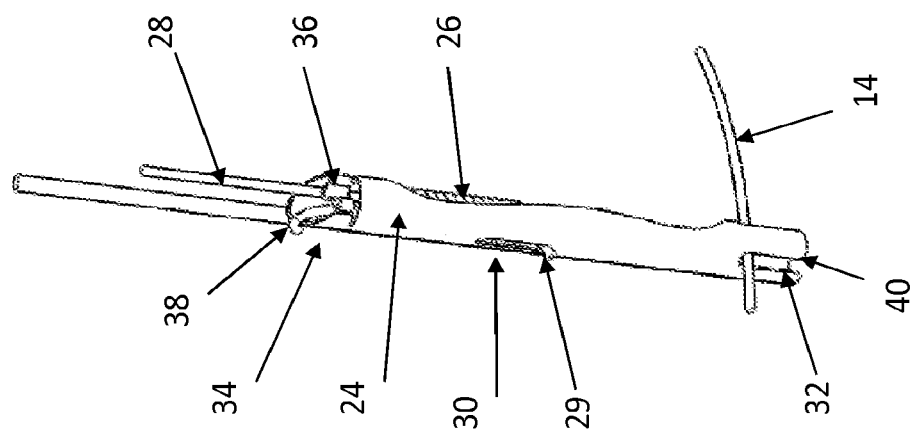

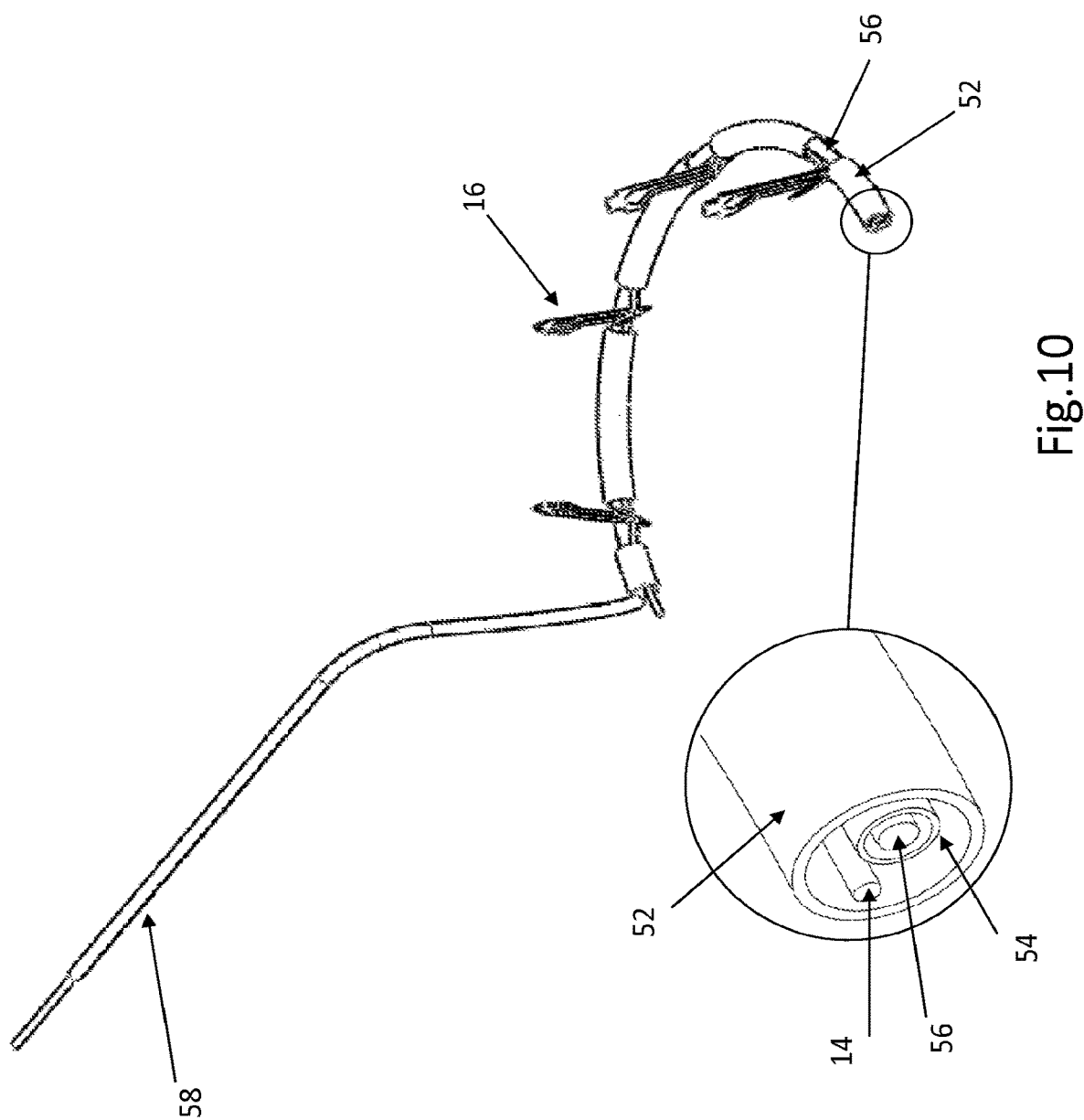

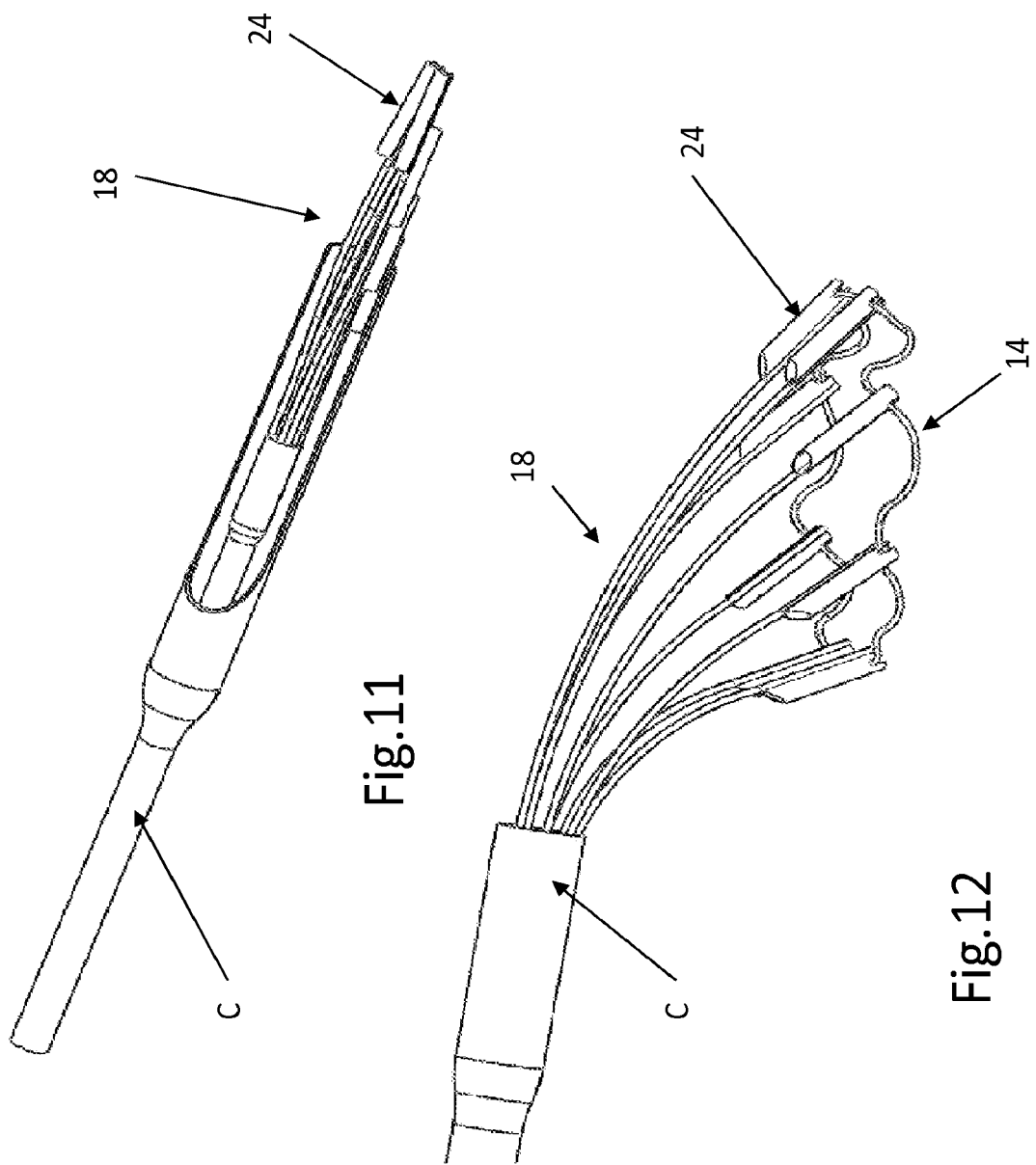

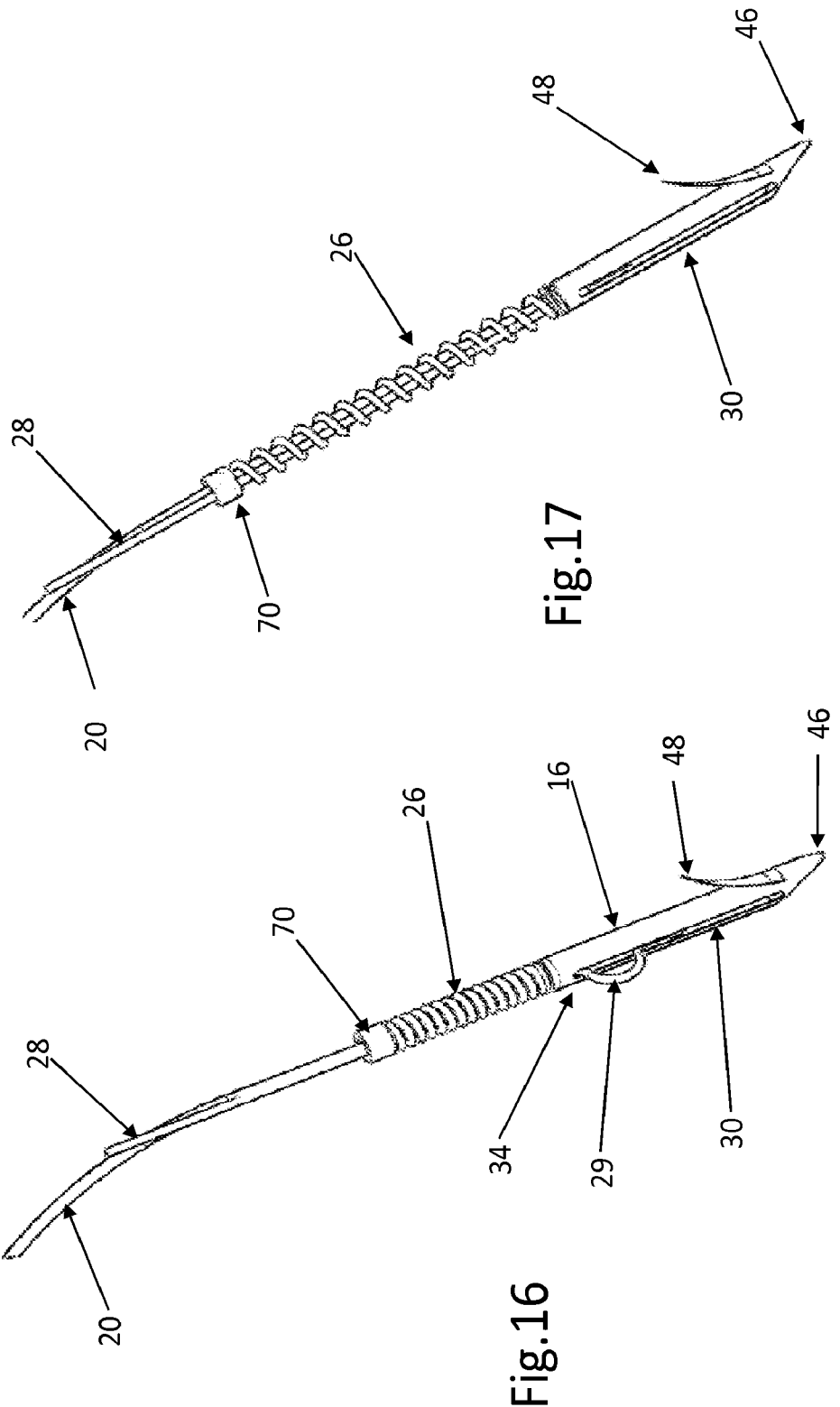

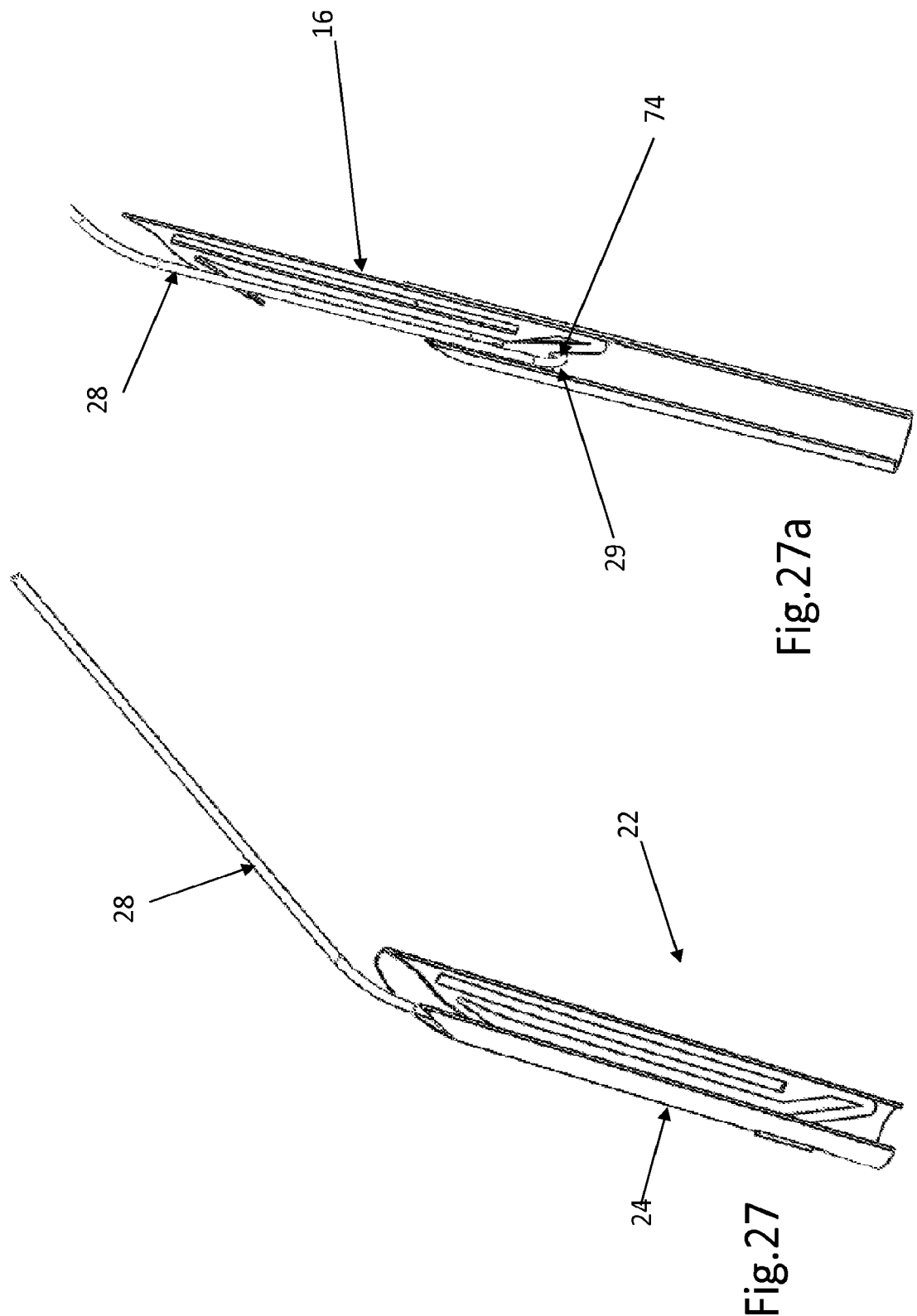

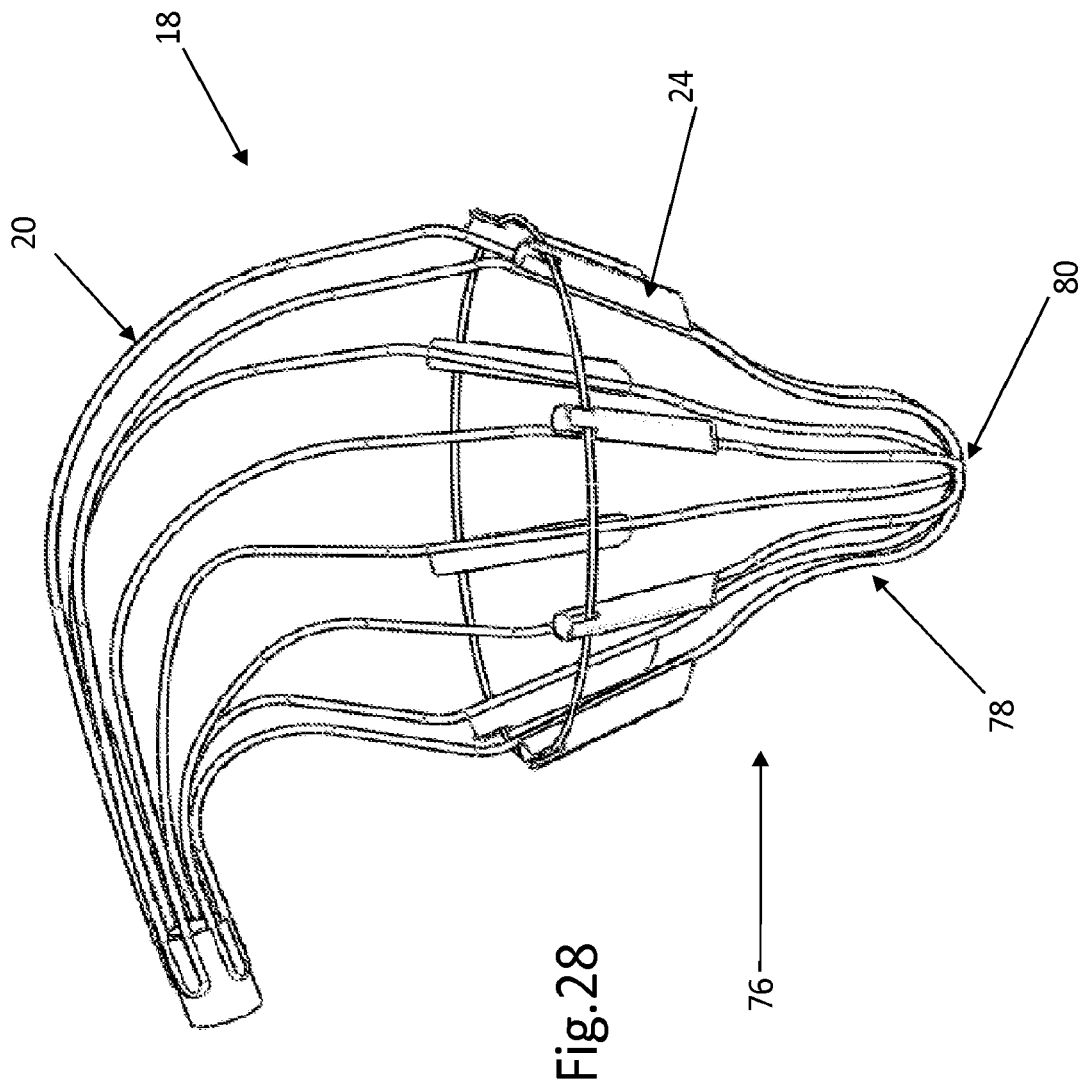

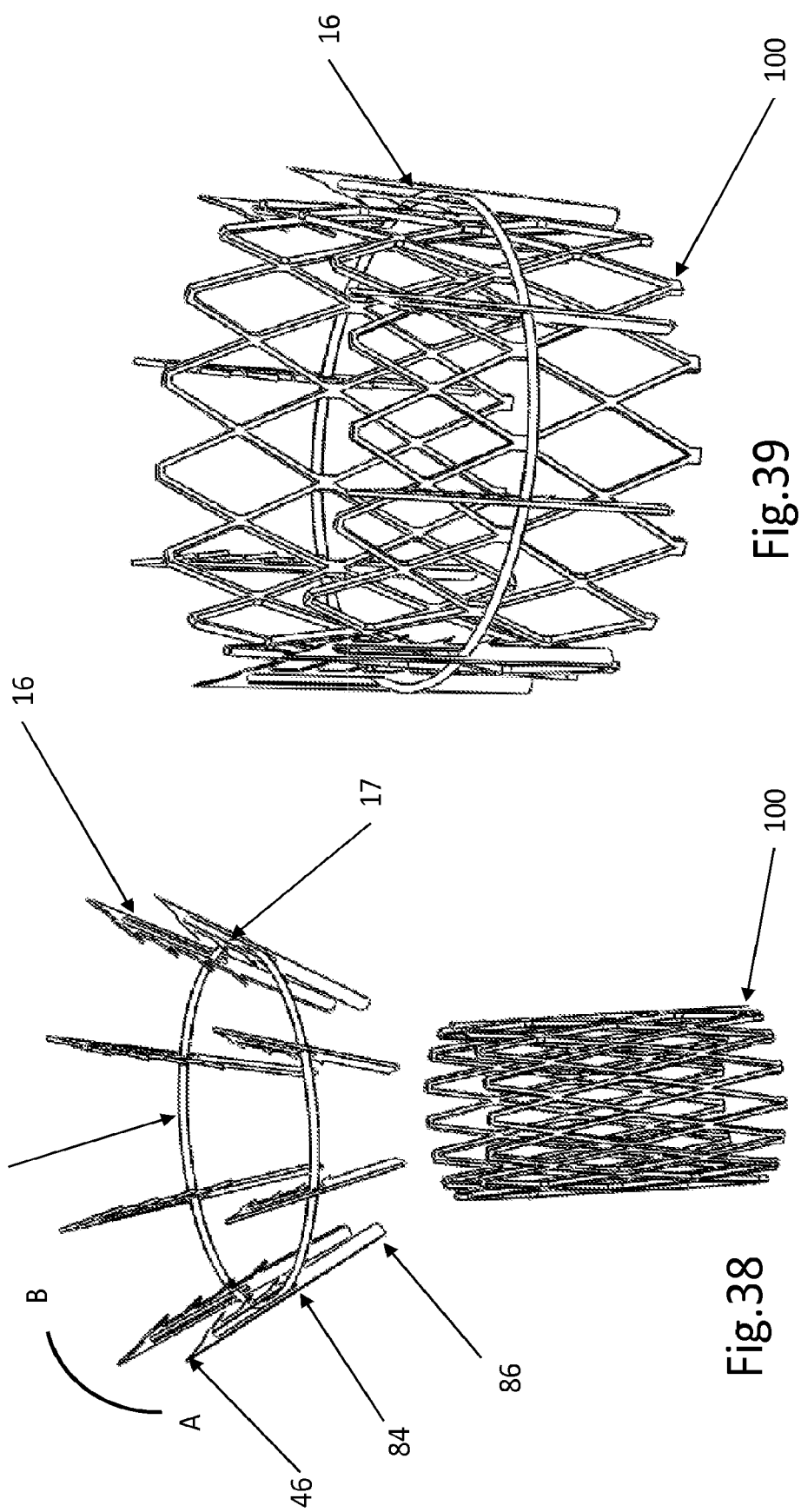

CARDIAC VALVE REPLACEMENT

CROSS REFERENCE TO RELATED APPLICATIONS

This Application is a continuation of U.S. patent application Ser. No. 14/364,060, filed Jun. 9, 2014, now U.S. Pat. No. 10,143,553, which is a national stage application under 35 U.S.C. § 371 of PCT/IB2012/057138, filed Dec. 10, 2012, which published as WO 2013/088327 and claims the benefit of U.S. Provisional Application 61/683,736, filed Aug. 16, 2012, and U.S. Provisional Application 61/569,304, filed Dec. 12, 2011. Each of the above-identified applications is incorporated herein by reference.

FIELD OF THE INVENTION

The present invention relates to medical devices, in particular, devices for repairing biological valves.

BACKGROUND OF THE INVENTION

The mitral valve is positioned in the heart left side, between the left atrium and the left ventricle. The most typical disease of the mitral valve is insufficiency or regurgitation which occurs when the valve leaflets do not coapt properly. Mitral valve repair by suturing a ring to reduce the annulus diameter is the procedure of choice to correct mitral regurgitation. With the use of current surgical techniques, most regurgitant mitral valves can be repaired or replaced with artificial valve prosthesis.

Currently, mitral valve repair requires an extremely invasive surgical approach that includes a sternotomy, cardiopulmonary bypass, cardiac arrest, and an incision in the heart itself to expose the mitral valve. Such procedure is associated with high morbidity and mortality. A percutaneous device that can effectively treat the disease without the need for open heart surgery could greatly improve patient benefit and may include other patients that currently cannot be treated with surgery being too old or frail for such invasive procedure.

Most current surgical practices for mitral valve repair involve mitral valve annuloplasty and/or mitral valve valvuloplasty.

Surgical annuloplasty is a technique aimed to reduce the size of the fibrous tissue at the base of the mitral valve, called the annulus. Sometimes the annulus becomes enlarged, enabling blood to back flow up into the left atrium, through the gap between the two separated valve leaflets. The repair is done with sutures to make the opening smaller, helping the two leaflets meet and co-apt again when the valve closes.

Surgical valvuloplasty is a technique aimed to ensure proper closure of the valve leaflets. Leaflet function can be impaired as the result of prolapse of a leaflet due to ruptured chordae. The leaflet reconstruction is done by leaflet resection and reshaped with sutures. In most cases both annuloplasty and valvuloplasty is needed in order to regain optimal mitral valve function.

Due to the invasive nature of the mitral valve surgery, and the high risks involved in the procedure, many heart failure patients are poor surgical candidates. Thus, less invasive methods and devices to reduce mitral valve regurgitation would make this therapy available to many more patients.

US2004/102839, US2004/1022840, U.S. Pat. No. 6,656,221, U.S. Pat. No. 6,718,985, U.S. Pat. No. 6,723,038 and US2004/073302 describe minimal invasive approaches to mitral valve annuloplasty, using percutaneous insertion of device into the left ventricle or into the coronary sinus, in order to decrease the annulus size.

U.S. Pat. No. 6,626,930 and U.S. Pat. No. 6,575,971 disclose a device and method of fastening two pieces of the valve leaflets together, improving competence of the valve.

US2004/243227, US2007/244554, US2008/262609, and US2009/0287304 describe percutaneous devices which attach to the valve annulus via anchoring mechanisms and contract, thereby reducing annulus diameter in a single step.

US2007/016286 discloses a transluminal collapsible heart valve designed to attach to the native annulus of the native regurgitating mitral valve and replace all in a single step. US2012/010700 provides a method for implanting a prosthetic valve apparatus that includes a one way valve and an expandable valve seating. The apparatus is anchored and secured in a newly created orifice near or at the center of the anterior valve leaflet.

Today it is possible to replace an aortic valve (the valve positioned between the left ventricle and aorta) with no surgery through newly developed percutaneous procedures. In these procedures an artificial collapsed valve is delivered through the arteries and positioned inside the diseased native valve, and then expanded to replace it. To date there is yet no acceptable analogous procedure that can do the same for the mitral or tricuspid valves.

Following the success of percutaneous replacement of the aortic valve, many attempts have been made to develop similar devices intended for percutaneous treatment of the mitral valve but due to the fact that this valve annulus is much bigger and amorphously shaped, and there are no lumen walls or calcific leaflets that may function as retaining surfaces like in the aortic valve, make it very difficult to prevent dislodgment of a valve expanded into place in the mitral position. Attaching a valve to the mitral annulus with anchoring features is very challenging for a percutaneous procedure and has not been very successful yet.

Devices that are attached to the mitral annulus and then collapsed to reduce its diameter need to be secured very tightly and accurately to the tissue in order to withhold the high forces that are required to reduce the annulus diameter.

Compared to the aortic valve percutaneous procedures, all the devices and procedures mentioned above have not been successful for the mitral valve yet.

SUMMARY OF THE INVENTION

The present invention relates to a device, method and kit for helping repair a biological valve and is particularly suited for repair of mitral, tricuspid and such valves, though not necessarily limited to such implementations.

In accordance with embodiments of one aspect of the invention there is provided an apparatus for performing a procedure on a heart valve annulus, the heart valve annulus having an original shape, the apparatus comprising: a tissue engaging member including a loop of wire configured to conform with at least a portion of the original shape when the loop of wire is deployed, and a plurality of anchors, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are arranged with respect to the loop of wire so that when the loop of wire is deployed the plurality of anchors are distributed about the loop of wire with the front ends of the plurality of anchors facing the heart valve annulus and with the loop of wire passing through the slots in the plurality of anchors. The apparatus further includes means for implanting the plurality of anchors into the heart valve annulus tissue so that the tissue engaging member becomes affixed to the heart valve annulus.

In some embodiments, the loop of wire comprises a closed loop. In some embodiments, the at least a portion of the original shape comprises at least a 270° portion of the original shape. In some embodiments, each of the plurality of anchors includes a barb that, subsequent to implantation, resists extraction from the heart valve annulus tissue in a backwards direction. In some embodiments, each of the plurality of anchors the back end of the slot is enlarged to form an eyelet. In some embodiments, in each of the plurality of anchors the slot begins near the front end of the anchor and ends near the back end of the anchor, and wherein, during implantation, forward motion of the plurality of anchors is limited when the ends of the slots encounter the loop of wire.

In some embodiments, the tissue engaging member further includes a plurality of tubes threaded onto the loop of wire between the plurality of anchors, wherein an outer surface of the tubes comprises a material that promotes tissue growth. In some embodiments, the tissue engaging member further includes a second loop of wire that is threaded through the inside the plurality of tubes, and wherein the second loop of wire comprises a closed loop.

In some embodiments, at least a portion of the second loop of wire is surrounded by a material that inhibits tissue growth. In some embodiments, the plurality of anchors comprises at least six anchors.

In some embodiments, the means for implanting comprises a plurality of compressed springs configured to, respectively, implant the plurality of anchors into the heart valve annulus tissue so that the tissue engaging member becomes affixed to the heart valve annulus. In some embodiments, the means for implanting comprises a plurality of pull wires configured to, respectively, implant the plurality of anchors into the heart valve annulus tissue so that the tissue engaging member becomes affixed to the heart valve annulus.

In some embodiments, the loop of wire comprises a closed loop, wherein each of the plurality of anchors includes a barb that, subsequent to implantation, resists extraction from the heart valve annulus tissue in a backwards direction, and wherein the plurality of anchors comprises at least six anchors. In some embodiments, the means for implanting comprises a plurality of compressed springs configured to, respectively, implant the plurality of anchors into the heart valve annulus tissue so that the tissue engaging member becomes affixed to the heart valve annulus. In some embodiments, the means for implanting comprises a plurality of pull wires configured to, respectively, implant the plurality of anchors into the heart valve annulus tissue so that the tissue engaging member becomes affixed to the heart valve annulus.

In some embodiments, the apparatus further comprises a catheter having a distal end; and a scaffold comprising a plurality of support arms configured to support the plurality of anchors in position adjacent to the heart valve annulus in a position at which the means for implanting can implant the plurality of anchors into the heart valve annulus tissue.

In some embodiments, the heart valve annulus is a mitral valve annulus, and the apparatus further comprises: a catheter having a distal end; and a scaffold comprising a plurality of support arms, wherein the scaffold is configured for deployment when the distal end of the catheter is positioned in the left atrium and the scaffold is further configured to support the plurality of anchors in position adjacent to the upper surface of the mitral valve annulus in a position at which the means for implanting can implant the plurality of anchors into the mitral valve annulus, wherein the catheter is configured to push the plurality of anchors towards the upper surface of the mitral valve annulus prior to implanting of the plurality of anchors.

In some embodiments, the apparatus further comprises a balloon configured for delivery in a deflated state via the catheter, and configured for inflation while at least part of the balloon is positioned the left ventricle, and wherein the catheter is configured to pull the balloon towards the mitral valve annulus prior to implanting of the plurality of anchors.

In some embodiments, the apparatus further comprises a balloon configured for delivery in a deflated state via the catheter, wherein when the balloon is inflated, the balloon guides the tissue engaging member into position for implantation into the mitral valve annulus.

In accordance with embodiments of another aspect of the invention there is provided a method for performing a procedure on a heart valve annulus, the heart valve annulus having an original shape. The method comprises the steps of: delivering a loop of wire to the vicinity of heart valve annulus so that the loop of wire conforms with at least a portion of the original shape; delivering a plurality of anchors to the vicinity of heart valve annulus, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are distributed about the loop of wire with the front ends of the plurality of anchors facing the heart valve annulus and with the loop of wire passing through the slots in the plurality of anchors; and implanting the plurality of anchors into the heart valve annulus.

In some embodiments, the loop of wire comprises a closed loop. In some embodiments, the at least a portion of the original shape comprises at least a 270° portion of the original shape. In some embodiments, each of the plurality of anchors the slot begins near the front end of the anchor and ends near the back end of the anchor, and wherein, during the implanting step, forward motion of the plurality of anchors is limited when the ends of the slots encounter the loop of wire.

In some embodiments, the method further comprises the step of delivering a plurality of tubes to the vicinity of heart valve annulus, wherein the plurality of tubes are threaded onto the loop of wire between the plurality of anchors and wherein an outer surface of the tubes comprises a material that promotes tissue growth.

In some embodiments, the method further comprises the step of delivering a second loop of wire to the vicinity of heart valve annulus that is threaded through the inside the plurality of tubes, wherein the second loop of wire comprises a closed loop. In some embodiments, the plurality of anchors comprises at least six anchors.

In some embodiments, the implanting step comprises driving the plurality of anchors into the heart valve annulus using a plurality of springs. In some embodiments, the implanting step comprises driving the plurality of anchors into the heart valve annulus using a plurality of pull wires. In some embodiments, the heart valve annulus is a mitral valve annulus, and the method further comprises the step of pressing the plurality of anchors towards an upper surface of the mitral valve annulus, wherein the pressing step is implemented prior to the implanting step and subsequent to the steps of delivering the loop of wire and delivering the plurality of anchors.

In some embodiments, the method further comprises the step of pulling an inflated balloon that is disposed at least partially in a left ventricle towards the mitral valve annulus, wherein the pulling step and the pressing step are performed simultaneously. In some embodiments, the method further comprises the step of inflating a balloon to guide the anchors into position for implantation into the mitral valve annulus.

In accordance with embodiments of another aspect of the invention there is provided an apparatus for performing a procedure on a mitral valve, the apparatus comprising: a tissue engaging member including a loop of wire configured to contact leaflets of the mitral valve when the loop of wire is deployed, wherein the loop of wire comprises a closed loop, and a plurality of anchors, each of the plurality of anchors having a pointy front end and a back end, each of the plurality of anchors having a slot that runs in a front-to-back direction, wherein the front ends of the plurality of anchors are configured for implantation into the leaflets in a forward direction and wherein the plurality of anchors are configured so that subsequent to implantation, the plurality of anchors resist extraction from the leaflets in a backwards direction, wherein the plurality of anchors are arranged with respect to the loop of wire so that when the loop of wire is deployed the plurality of anchors are distributed about the loop of wire with the front ends of the plurality of anchors facing the leaflets and with the loop of wire passing through the slots in the plurality of anchors. The apparatus further includes means for implanting the plurality of anchors into the leaflets so that the tissue engaging member becomes affixed to the leaflets.

In some embodiments, each of the plurality of anchors includes a barb that, subsequent to implantation, resists extraction from the leaflets in a backwards direction. In some embodiments, each of the plurality of anchors the slot begins near the front end of the anchor and ends about halfway between the front end of the anchor and the back end of the anchor, and during implantation, forward motion of the plurality of anchors is limited when the ends of the slots encounter the loop of wire.

In some embodiments, the plurality of anchors comprises at least six anchors. In some embodiments, the means for implanting comprises a plurality of compressed springs configured to, respectively, implant the plurality of anchors into the leaflets so that the tissue engaging member becomes affixed to the leaflets.

In some embodiments, the means for implanting comprises a plurality of pull wires configured to, respectively, implant the plurality of anchors into the leaflets so that the tissue engaging member becomes affixed to the leaflets.

In some embodiments, the apparatus further comprises a catheter having a distal end; and a scaffold comprising a plurality of support arms configured to support the plurality of anchors in position adjacent to the leaflets in a position at which the means for implanting can implant the plurality of anchors into the leaflets.

In some embodiments, the apparatus further comprises: a catheter having a distal end; and a scaffold comprising a plurality of support arms, wherein the scaffold is configured for deployment when the distal end of the catheter is positioned in the left ventricle and the scaffold is further configured to support the plurality of anchors in position adjacent to the leaflets in a position at which the means for implanting can implant the plurality of anchors into the leaflets, wherein the catheter is configured to push the plurality of anchors towards the leaflets prior to implanting of the plurality of anchors.

In some embodiments, the apparatus further comprises: a catheter having a distal end; and a scaffold comprising a plurality of support arms, wherein the scaffold is configured for deployment when the distal end of the catheter is positioned in the left ventricle and the scaffold is further configured to support the plurality of anchors in position adjacent to the leaflets in a position at which the means for implanting can implant the plurality of anchors into the leaflets, wherein the catheter is configured to pull the plurality of anchors towards the leaflets prior to implanting of the plurality of anchors.

In accordance with embodiments of another aspect of the invention there is provided a method for performing a procedure on a mitral valve comprising the steps of: delivering a loop of wire to a vicinity of leaflets of the mitral valve, wherein the loop of wire comprises a closed loop; delivering a plurality of anchors to the vicinity of the leaflets, each of the plurality of anchors having a pointy front end and a back end, each of the plurality of anchors having a slot that runs in a front-to-back direction, wherein the front ends of the plurality of anchors are configured for implantation into the leaflets in a forward direction and wherein the plurality of anchors are configured so that subsequent to implantation, the plurality of anchors resist extraction from the leaflets in a backwards direction, wherein the plurality of anchors are distributed about the loop of wire with the front ends of the plurality of anchors facing the leaflets and with the loop of wire passing through the slots in the plurality of anchors; and implanting the plurality of anchors into the leaflets.

In some embodiments, each of the plurality of anchors the slot begins near the front end of the anchor and ends about halfway between the front end of the anchor and the back end of the anchor, and wherein, during the implanting step, forward motion of the plurality of anchors is limited when the ends of the slots encounter the loop of wire.

In some embodiments, the plurality of anchors comprises at least six anchors. In some embodiments, the implanting step comprises driving the plurality of anchors into the leaflets using a plurality of springs. In some embodiments, the implanting step comprises driving the plurality of anchors into the leaflets using a plurality of pull wires.

In some embodiments, the method further comprises the step of pressing the plurality of anchors towards the leaflets, wherein the pressing step is implemented prior to the implanting step and subsequent to the steps of delivering the loop of wire and delivering the plurality of anchors.

In accordance with embodiments of another aspect of the invention there is provided an apparatus for cinching a heart valve annulus, the heart valve annulus having an original shape, the apparatus comprising: a tissue engaging member including a first loop of wire configured to conform with at least a portion of the original shape when the first loop of wire is deployed, a plurality of anchors, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are arranged with respect to the first loop of wire so that when the first loop of wire is deployed the plurality of anchors are distributed about the first loop of wire with the front ends of the plurality of anchors facing the heart valve annulus and with the first loop of wire passing through the slots in the plurality of anchors, a plurality of tubes threaded onto the first loop of wire between the plurality of anchors, wherein an outer surface of the tubes comprises a material that promotes tissue growth, and a second loop of wire that is threaded through the inside the plurality of tubes, the second loop of wire having two ends that are configured so that when the tissue engaging member is affixed to the heart valve annulus, pulling the two ends will cinch the heart valve annulus; and means for implanting the plurality of anchors into the heart valve annulus tissue so that the tissue engaging member becomes affixed to the heart valve annulus.

In some embodiments, at least a portion of the second loop of wire is surrounded by a material that inhibits tissue growth. In some embodiments, the at least a portion of the original shape comprises at least a 270° portion of the original shape. In some embodiments, wherein each of the plurality of anchors includes a barb that, subsequent to implantation, resists extraction from the heart valve annulus tissue in a backwards direction. In some embodiments, in each of the plurality of anchors the back end of the slot is enlarged to form an eyelet. In some embodiments, each of the plurality of anchors the slot begins near the front end of the anchor and ends near the back end of the anchor, and wherein, during implantation, forward motion of the plurality of anchors is limited when the ends of the slots encounter the first loop of wire.

In some embodiments, the plurality of anchors comprises at least six anchors. In some embodiments, the means for implanting comprises a plurality of compressed springs configured to, respectively, implant the plurality of anchors into the heart valve annulus tissue so that the tissue engaging member becomes affixed to the heart valve annulus. In some embodiments, the means for implanting comprises a plurality of pull wires configured to, respectively, implant the plurality of anchors into the heart valve annulus tissue so that the tissue engaging member becomes affixed to the heart valve annulus.

In some embodiments, each of the plurality of anchors includes a barb that, subsequent to implantation, resists extraction from the heart valve annulus tissue in a backwards direction, wherein the plurality of anchors comprises at least six anchors, and wherein the means for implanting comprises a plurality of compressed springs configured to, respectively, implant the plurality of anchors into the heart valve annulus tissue so that the tissue engaging member becomes affixed to the heart valve annulus. In some embodiments, each of the plurality of anchors includes a barb that, subsequent to implantation, resists extraction from the heart valve annulus tissue in a backwards direction, wherein the plurality of anchors comprises at least six anchors, and wherein the means for implanting comprises a plurality of pull wires configured to, respectively, implant the plurality of anchors into the heart valve annulus tissue so that the tissue engaging member becomes affixed to the heart valve annulus.

In some embodiments, the apparatus further comprises: a catheter having a distal end; and a scaffold comprising a plurality of support arms configured to support the plurality of anchors in position adjacent to the heart valve annulus in a position at which the means for implanting can implant the plurality of anchors into the heart valve annulus tissue.

In some embodiments, the heart valve annulus is a mitral valve annulus, and the apparatus further comprises: a catheter having a distal end; and a scaffold comprising a plurality of support arms, wherein the scaffold is configured for deployment when the distal end of the catheter is positioned in the left atrium and the scaffold is further configured to support the plurality of anchors in position adjacent to the upper surface of the mitral valve annulus in a position at which the means for implanting can implant the plurality of anchors into the mitral valve annulus, wherein the catheter is configured to push the plurality of anchors towards the upper surface of the mitral valve annulus prior to implanting of the plurality of anchors.

In some embodiments, the apparatus further comprises a balloon configured for delivery in a deflated state via the catheter, and configured for inflation while at least part of the balloon is positioned the left ventricle, and wherein the catheter is configured to pull the balloon towards the mitral valve annulus prior to implanting of the plurality of anchors.

In some embodiments, the apparatus further comprises a balloon configured for delivery in a deflated state via the catheter, wherein when the balloon is inflated, the balloon guides the tissue engaging member into position for implantation into the mitral valve annulus.

In accordance with embodiments of another aspect of the invention there is provided a method for cinching a heart valve annulus, the heart valve annulus having an original shape. The method comprising the steps of: delivering a first loop of wire to the vicinity of heart valve annulus so that the first loop of wire conforms with at least a portion of the original shape; delivering a plurality of anchors to the vicinity of heart valve annulus, each of the plurality of anchors having a pointy front end and a back end, each of the plurality of anchors having a slot that runs in a front-to-back direction, wherein the front ends of the plurality of anchors are configured for implantation into heart valve annulus tissue in a forward direction and wherein the plurality of anchors are configured so that subsequent to implantation, the plurality of anchors resist extraction from the heart valve annulus tissue in a backwards direction, wherein the plurality of anchors are distributed about the first loop of wire with the front ends of the plurality of anchors facing the heart valve annulus and with the first loop of wire passing through the slots in the plurality of anchors; delivering a plurality of tubes to the vicinity of heart valve annulus, wherein the plurality of tubes are threaded onto the first loop of wire between the plurality of anchors and wherein an outer surface of the tubes comprises a material that promotes tissue growth; delivering a second loop of wire to the vicinity of heart valve annulus, wherein the second loop of wire is threaded through the inside the plurality of tubes and has a first end and a second end; implanting the plurality of anchors into the heart valve annulus; and cinching the second loop of wire by pulling on the first end and the second end.

In some embodiments, the at least a portion of the original shape comprises at least a 270° portion of the original shape. In some embodiments, in each of the plurality of anchors the slot begins near the front end of the anchor and ends near the back end of the anchor, and wherein, during the implanting step, forward motion of the plurality of anchors is limited when the ends of the slots encounter the first loop of wire. In some embodiments, the plurality of anchors comprises at least six anchors.

In some embodiments, the implanting step comprises driving the plurality of anchors into the heart valve annulus using a plurality of springs. In some embodiments, the implanting step comprises driving the plurality of anchors into the heart valve annulus using a plurality of pull wires.

In some embodiments, the heart valve annulus is a mitral valve annulus, and the method further comprises the step of pressing the plurality of anchors towards an upper surface of the mitral valve annulus, wherein the pressing step is implemented prior to the implanting step and subsequent to the steps of delivering the first loop of wire and delivering the plurality of anchors.

In some embodiments, the method further comprising the step of pulling an inflated balloon that is disposed at least partially in a left ventricle towards the mitral valve annulus, wherein the pulling step and the pressing step are performed simultaneously.

In some embodiments, the method further comprises the step of inflating a balloon to guide the anchors into position for implantation into the mitral valve annulus.

BRIEF DESCRIPTION OF THE DRAWINGS

The present invention will be understood and appreciated more fully from the following detailed description taken in conjunction with the appended drawings in which:

FIGS. 4-6 are perspective views of an anchor launching mechanism of the device of FIG. 1;

FIGS. 8-10 are perspective views of an another embodiment of the tissue engaging member;

FIGS. 11 and 12 are perspective views of an exemplary delivery system for the present device;

FIGS. 15-17 are perspective views of additional embodiments of anchors;

FIGS. 23-27 and 27a are perspective views of further embodiments of anchor launching mechanisms;

FIGS. 28-30 are perspective views of implant deployment mechanisms;

FIGS. 35-39 are perspective views illustrating the device in use in conjunction with an implantable device;

Figure 1:
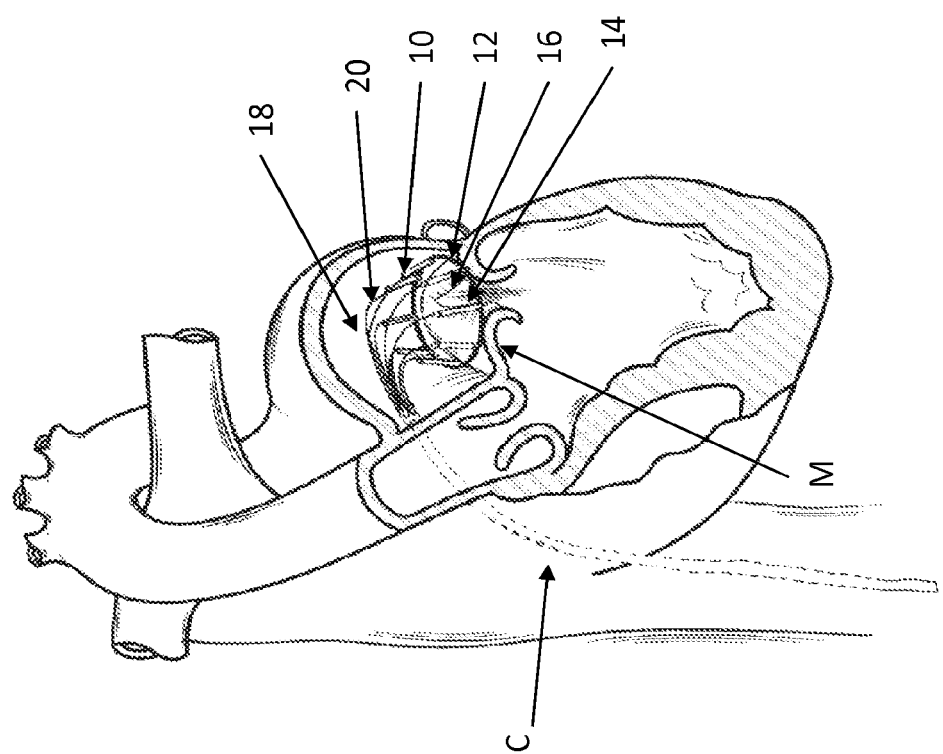
FIG. 1 is a front partial cut-away view of an embodiment of a heart valve repair device of the present invention.

The following detailed description of embodiments of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DESCRIPTION OF EMBODIMENTS OF THE INVENTION

A heart valve repair device comprising an implant and delivery system is delivered into the heart in four sequential stages: In the first stage the implant and support scaffold are advanced in a collapsed configuration inside a capsule through the vascular system to the valve annulus (preferably the Mitral annulus but can be also the Tricuspid annulus). In the second stage after positioning the capsule close to the annulus a support scaffold is pushed outside of the capsule and the implant which is attached to the scaffold is spread into a round or D shape circumferential ring onto the valve annulus in 3 optional ways:

1) On the inflow side of the valve with attachment anchors pointing from the atrium side to the ventricle side;
2) On the inflow side of the valve with attachment anchors pointing from the ventricle side to the atrium side; and
3) On the outflow side of the valve with attachment anchors pointing from the ventricle side to the atrium side.

In the third stage after the implant is spread out, all the anchors are launched into the tissue at once or in a sequential manner and affix the implant to the tissue. The same action also separates the implant from the support scaffold and delivery system. In the fourth stage the scaffold is retracted and collapsed back into the delivery capsule and the delivery system is withdrawn out of the body.

It is important to note that in some embodiments the spread implant conforms at least partially to the valve annulus shape, and in some embodiments the spread implant does not conform at all to the valve annulus shape, but is just affixed to the valve leaflets and is retained there for a few minutes until a valve prosthesis is deployed into it as will be described later on.

After the implant is attached to the valve tissue it is possible to treat the valve insufficiency in 5 optional ways:

1) By direct annuloplasty which impose cinching of the implant attached to the valve annulus, hence reducing the annulus diameter and improving valve leaflets coaptation;
2) By restricting annulus dilatation over time due to the constant perimeter of the implant which is attached to the valve annulus and gets embedded into the tissue over time through tissue growth;
3) By facilitating a support ring for valve prosthesis to be implanted at a later procedure after the implant which is attached to the valve annulus gets embedded into the tissue over time through tissue growth;
4) By performing annuloplasty at a later stage in a different procedure weeks or months later after the implant which is attached to the valve annulus gets embedded into the tissue over time through tissue growth; and 5) By facilitating a support ring for valve prosthesis that can be implanted into the ring during the same procedure right after the ring is attached to the valve leaflets.

Illustrative embodiments of the invention are described below. In the interest of clarity, not all features/components of an actual implementation are necessarily described.

FIG. 1 shows an embodiment of a mitral valve adjustment/repair implant 10 of the present invention, implanted onto a bio-valve, exemplified by mitral valve M of the heart. Implant 10 comprises: a tissue engaging member 12, comprising a loop 14 of wire and a plurality of tissue anchors 16 associated with the loop and having and an elongated slot 17 (FIG. 5); a scaffold or implant positioning device 18, in this embodiment comprising plurality of support arms 20; and an anchor launching mechanism 22 (FIGS. 2-7). Implant 10 is typically positioned in proximity of the mitral valve M via a delivery catheter C. The loop 14 of wire is preferably made of metal wire, but in alternative embodiments the wire may be a non-metallic material. Note that as used herein, "wire" includes metal and/or non-metallic materials.

Figure 2:
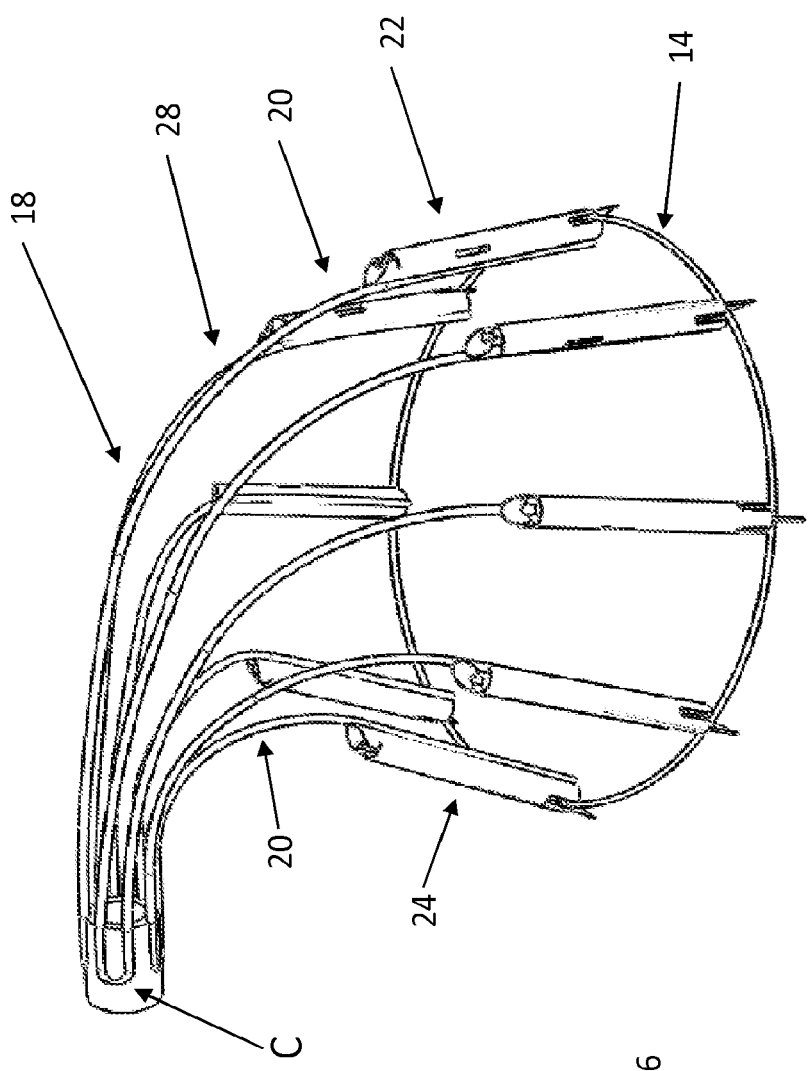
FIG. 2 is an enlarged perspective view of the device of FIG. 1.
Figure 3:
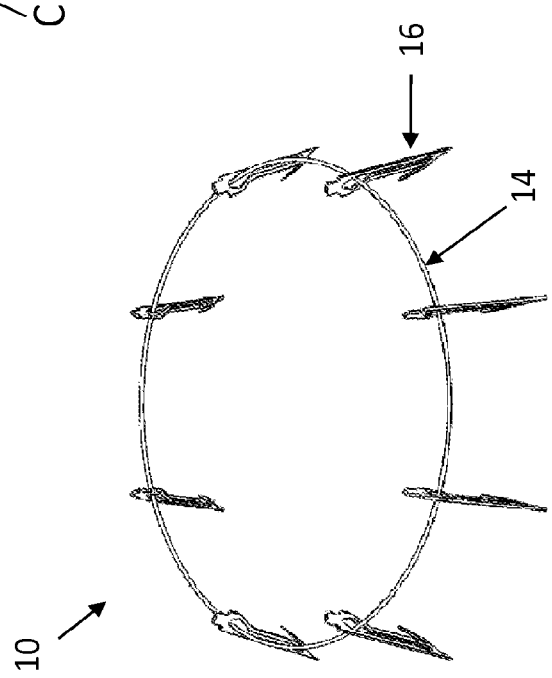
FIG. 3 is a perspective view of an implant or tissue engaging member of the present device.

FIG. 2 shows an enlarged view of the device in FIG. 1 illustrating anchor launching mechanism 22 in a ready for deployment (launching) and deployed state, respectively; Elongated slot 17 of anchors 16 allow loop 14 to be retained by (operably attached to) the anchors—which will be explained further herein below. FIG. 3 shows an embodiment of implant 10 in its configuration when implanted, as will be discussed further below.

Figure 6:
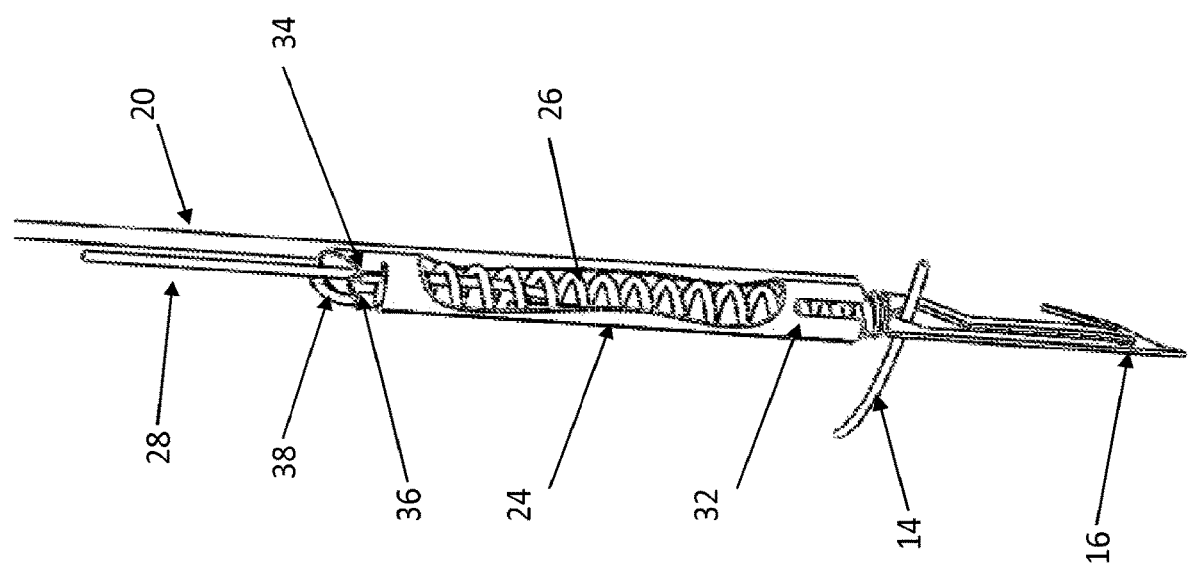

FIGS. 4-6 show details of anchor launching mechanism 22, which comprises a housing 24, typically cylindrical; an anchor launching biasing mechanism, such as coil spring 26 disposed within the housing; and a spring actuator wire 28, having a bent distal end 29, passing through elongated slot 17 and protruding through a window 30 of housing 24. Bent distal end 29 maintains spring 26 is a compressed configuration. Actuator wire 28 passes longitudinally/coaxially through coil spring 26. Implant support arms 20 are respectively attached to housings 24, for example by welding. It should be noted that actuator wire 28 can be made of any appropriate material and is not limited to metal.

Housing 24 has an open end 32 and a spring retention end 34, which in some embodiments comprises a crimped portion 36 or other such spring retention mechanism, to provide a launching base for spring 26. In some embodiments, to prevent spring 26 from being ejected from (falling out of) housing 24, spring has a hooked proximal end 38 adapted to hook at retention end 34 of the housing. As can be seen, loop 14 is threaded through each elongated slot 17 of tissue anchors 16. As best seen in FIG. 4, in some embodiments, housing 24 has a pair of elongated recesses 40 at open end 32 whereby loop 14 can pass. FIGS. 4 and 5 show anchors 16 in a pre-launch state where spring 26 is compressed, and FIG. 6 shows the anchors in a launched state with the spring in its normally expanded configuration.

As shown, tissue anchors 16 are typically spaced apart all along loop 14 and loop 14 is threaded through elongated slot 17, allowing the tissue anchor to move (be launched), typically more or less perpendicular (although in some embodiments at an angle) with respect to the loop. It should be noted that loop 14 can be made of any appropriate material and is not limited to metal. Note that while eight anchors are depicted in all the illustrated embodiments, the number of anchors can be varied. Preferably at least six anchors are used.

Figure 7A:
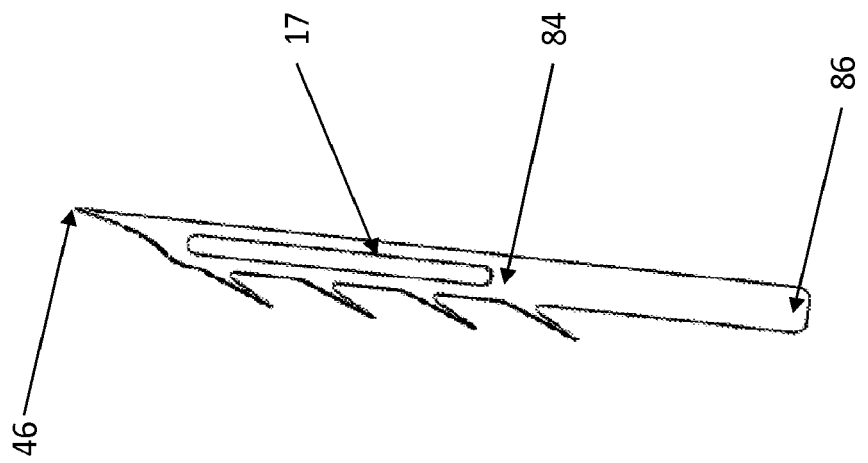
FIGS. 7 and 7a are perspective views of anchors of the present device.
Figure 7:
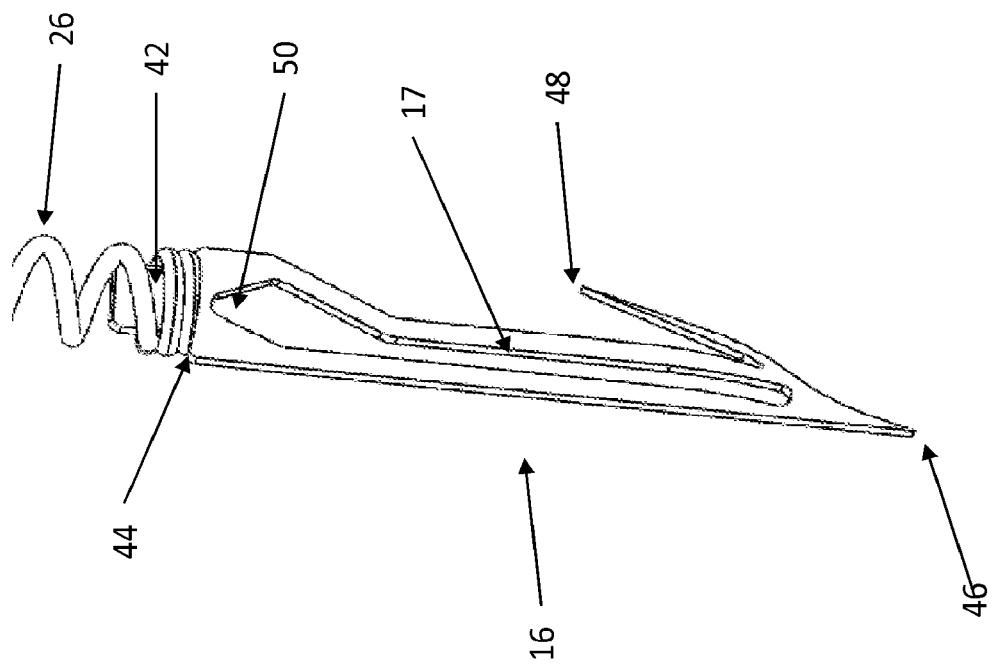

With reference to FIG. 7, in some embodiments, each anchor 16 has a proximal portion 42 including a spring interfacing portion exemplified by a pair of fiat shoulders 44. Anchors 16 also have a pointy front end 46, typically with one or more barbs 48. After an anchor is implanted in the forward direction, the barbs 48 resist extraction of the anchor 16 in a backwards direction. In some embodiments, elongated slot 17 has a relatively large or bulbous open portion or eyelet 50 adjacent proximal portion 42, which can be useful to provide additional space for bent distal end 29 to pass through the elongated slot along with loop 14.

Figure 8:
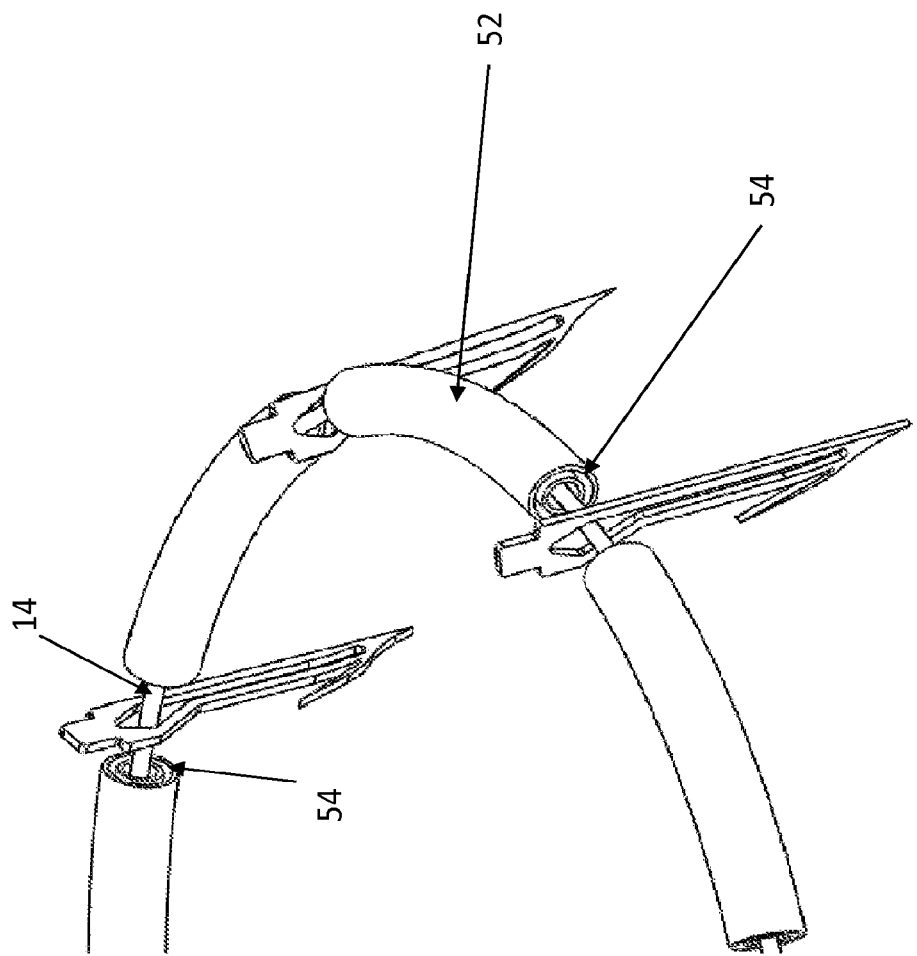
Figure 9:
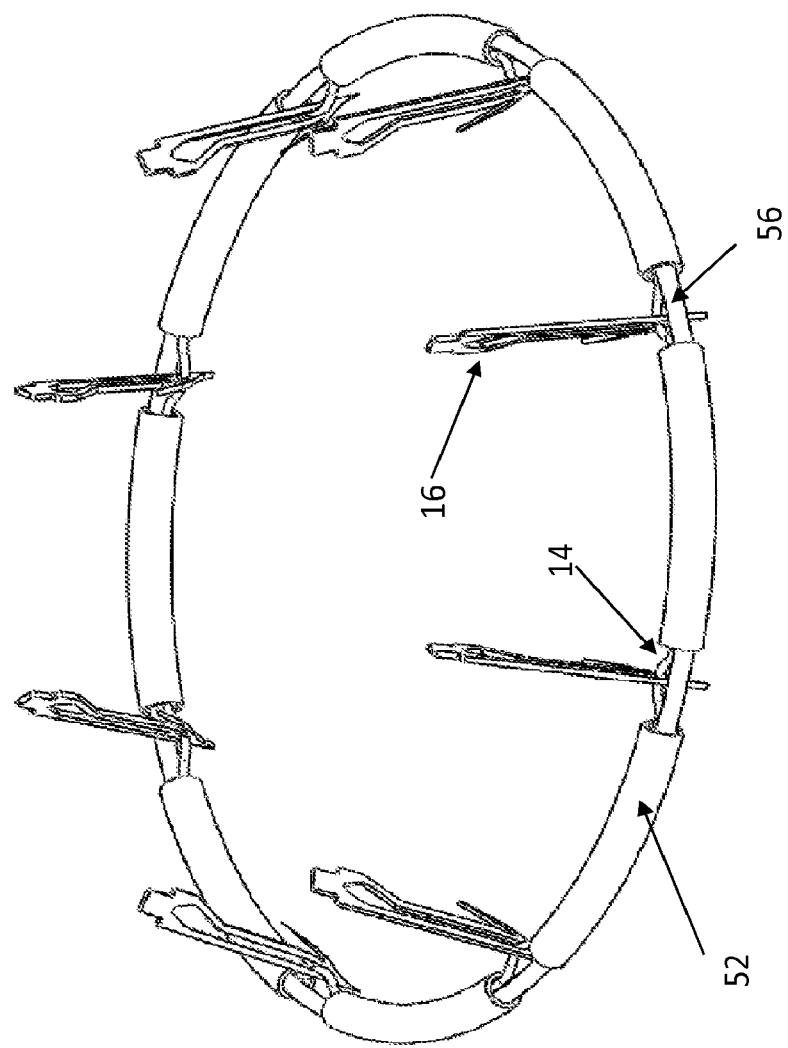

FIGS. 8-10 shows a modification of the implant wherein loop 14 has a plurality of tissue growth-promotion tubes 52 coaxially surrounding the loop between anchor positions. In some embodiments, tissue growth-promotion tubes 52 have respective tissue growth inhibiting liners or surfaces 54 (FIG. 10). Tissue growth-promotion tubes 52 are made of a material and/or substance adapted to promote and facilitate the growth of tissue thereon, for example an appropriate fabric or coating. If indeed in the form of liners, tissue growth inhibiting liners 54 are disposed tissue growth-promotion tubes 52, e.g. coaxially, and include tissue growth inhibiting material/substance.

FIGS. 9 and 10 additionally show another embodiment wherein there are two loops, the aforementioned loop 14 and a relatively sturdy auxiliary loop 56 to provide additional robustness to the implant if so desired. FIG. 10 shows a modification wherein auxiliary loop further includes a proximal portion 58 that can be used to position the implant 10, in addition to or in place of the above mentioned implant positioning device 18.

Operation: implant 10 is deployed to a position adjacent the bio-valve (e.g. Mitral valve M) via/through delivery catheter C (see FIGS. 11 and 12; and also FIGS. 1 and 2). When implant 10 is appropriately located, using support arms 20 and\or auxiliary loop 56 with its proximal portion 58, actuator wire 28 of each anchor launching mechanism 22 is retracted thereby withdrawing their bent distal ends 29 from respective windows 30 of housings 24. As a result, springs 26 are released from their compressed state to their expanded state thereby launching tissue anchors 16 into the bio-valve tissue. Typically, pointy end 46 of each anchor 16 enters the tissue, and barbs 48 help to prevent inadvertent detachment of the anchors.

Figure 13:
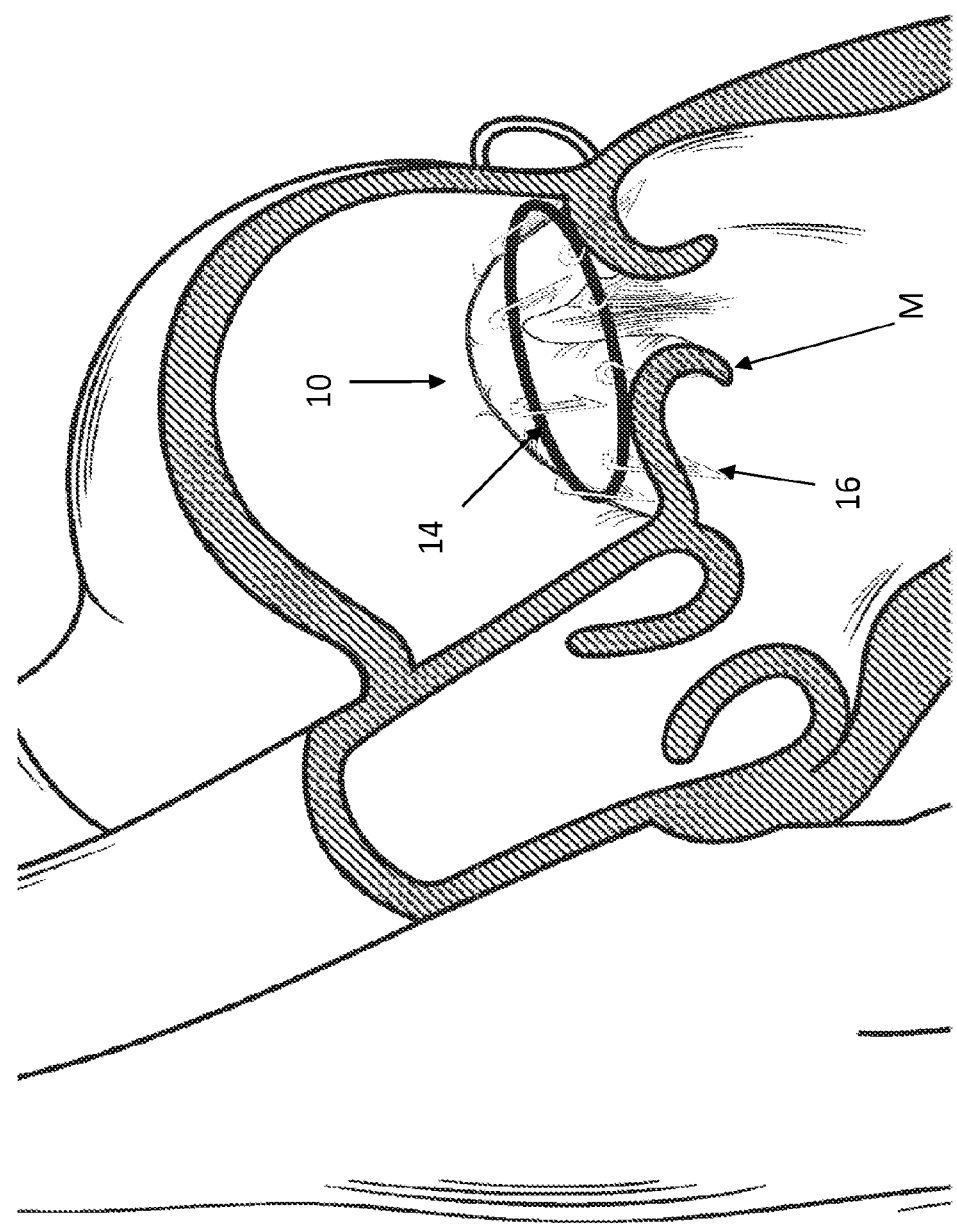
FIG. 13 is a front partially cut-away view of a heart with the implant affixed to a mitral valve from above the valve.

FIG. 13 illustrates implant 10 connected to the tissue of mitral valve M of the heart after the launching of tissue anchors 16 into the tissue. Implant 10 is positioned on the top of the mitral valve M, as a result of being inserted into the heart in a manner such as shown in FIG. 1, and anchors 16 face generally downward. After the implantation natural tissue growth start to occur all around the parts of implant 10 that are within the tissue notably the anchors, and later on tissue growth will cover also parts of the implant at close proximity to the tissue surface. When tissue growth fills the anchors slot 17 they become mechanically locked within the tissue, and over time the entire implant 10 will get embedded in the valve annulus tissue. Since the implant is largely comprised of loop 14 which is made of non elastic substance, further annulus dilatation over time due to progression of the valve regurgitation disease is prevented.

Figure 14:
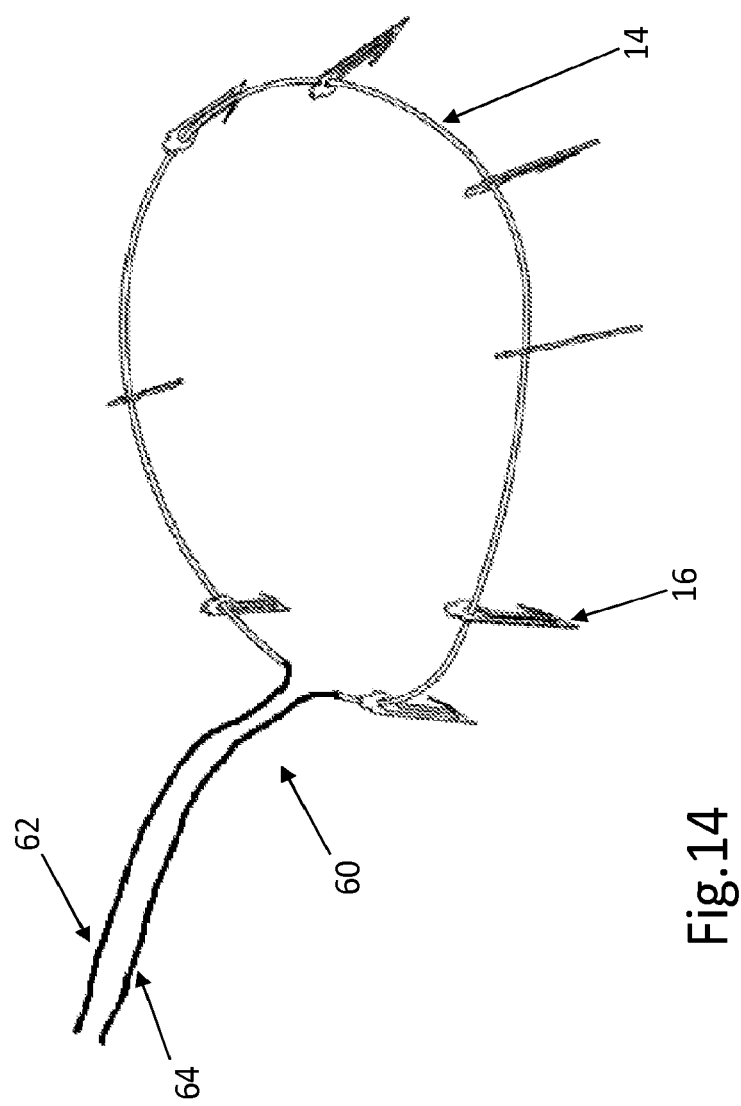
FIG. 14 is a perspective view of a cinching mechanism of the device.

With reference to FIG. 14, in some embodiments, the implant further comprises a cinching mechanism 60, for example wherein loop 14 is not in a closed loop configuration rather has generally adjacent free ends 62 and 64. The ring-like portion of loop 14 passes through elongated slots 17 of anchors 16 (and in suitable embodiments, through tissue growth-promotion tubes 52), as before. After sufficient tissue grows on implant 10, which typically takes one week to several months, depending on the tissue growth rate, the implant may be cinched via pulling on one or both of the free ends 62 and/or 64 to reduce the diameter of tissue engaging member 12, (however, in some implementations of the operation, cinching action is not required, and could be excluded from procedure). Free ends 62 and 64 may extend outside the patient's body or remain under the skin at the upper portion of the chest, much like pace maker leads. The tissue growth causes implant 10 to be embedded and integrated to the valve annulus. In addition, tissue growth within elongated slot 17 helps secure anchors 16 and prevents the implant from being dislodged from the valve annulus.

FIG. 14 further illustrates a D-shaped loop 14, in contrast to the circular or oval shaped loops illustrated in the aforementioned figures. D-shaped loop 14 is particularly suited for use with a human mitral heart valve. In this regard, it should be understood that loop 14 can be configured by choice or design to appropriately correspond to the particular bio-valve for which repair is required.

Figure 15:
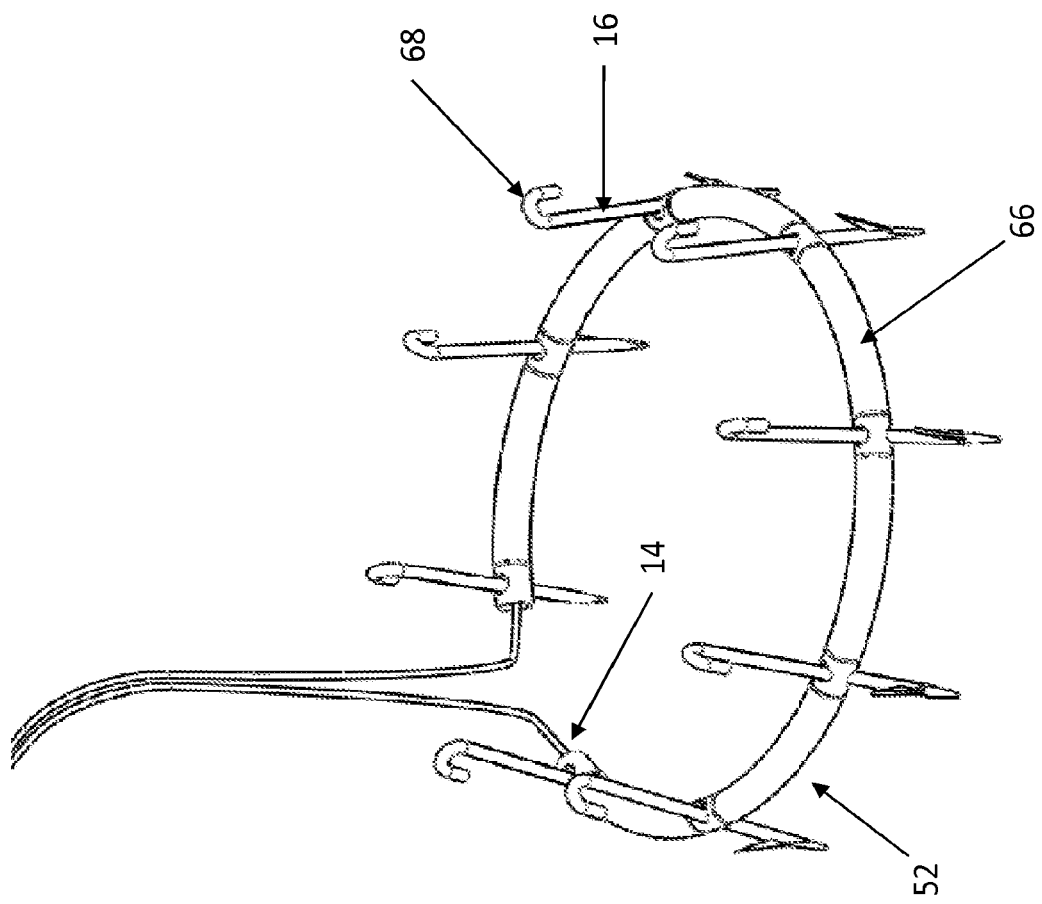

FIG. 15 shows another embodiment wherein instead of anchors 16 engaging loop 14 via elongated slot 17, the anchors pass thru a coaxial tube 66 coaxially surrounding the loop—the tube could be, for example a tissue growth promotion tube such as tissue growth-promotion tubes 52. Retention of anchors 16 with coaxial tube 66 is aided by a retention hook 68 at the proximal end of the anchors.

FIGS. 16 and 17 depict an embodiment where anchor 16 has a cylindrical shape, similar to housing 24 and no such housing is required. In this case spring 26 is held in compression between end 34 of cylindrical anchor 16 and a spring launching base, exemplified by a launching base ring 70, attached to implant support arms 20. End 34 now provides the function of the aforementioned flat shoulders 44; and launching base ring provides the function of the aforementioned crimped portion 36. When actuator wire 28 is retracted, its bent distal end 29 (here, illustrated in the form of a half-loop) is retracted from window 30 thereby releasing cylindrical anchor 16 so that spring 26 expands to launch the anchor.

Figure 19:
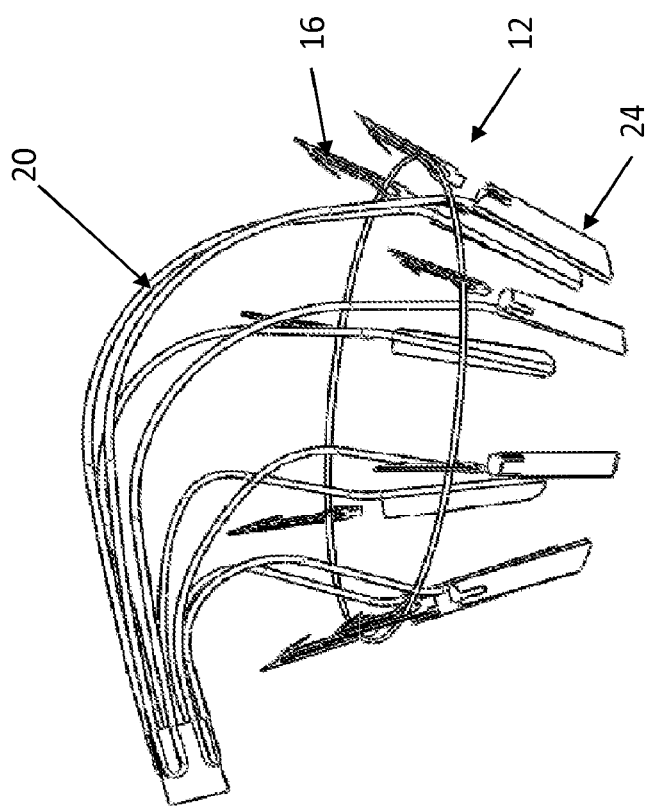
FIGS. 18 and 19 are perspective views of embodiments of anchor launching mechanisms.
Figure 18:
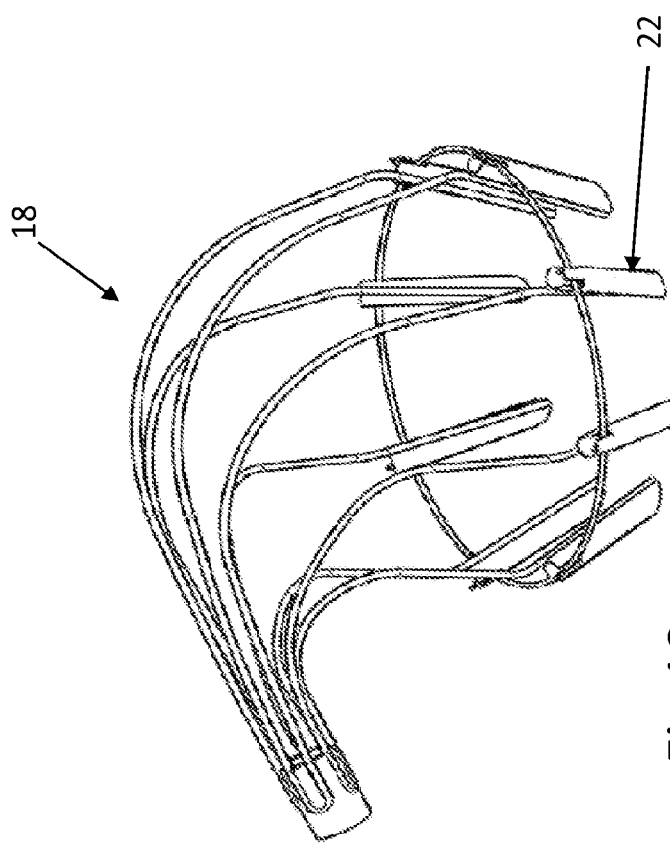

FIGS. 18 and 19 shows implant positioning device 18 configured, mutatis mutandis, wherein anchor launching mechanism 22 is adapted to launch anchors 16 into the tissue in a generally upward direction (i.e. from the ventricle side to the atrium side). This embodiment is particularly useful in the case where the tissue engaging member 12 serves as a support to prevent dislodgement of a valve prosthesis that can be expanded into it right after the tissue engaging member 12 has been deployed.

Figure 20:
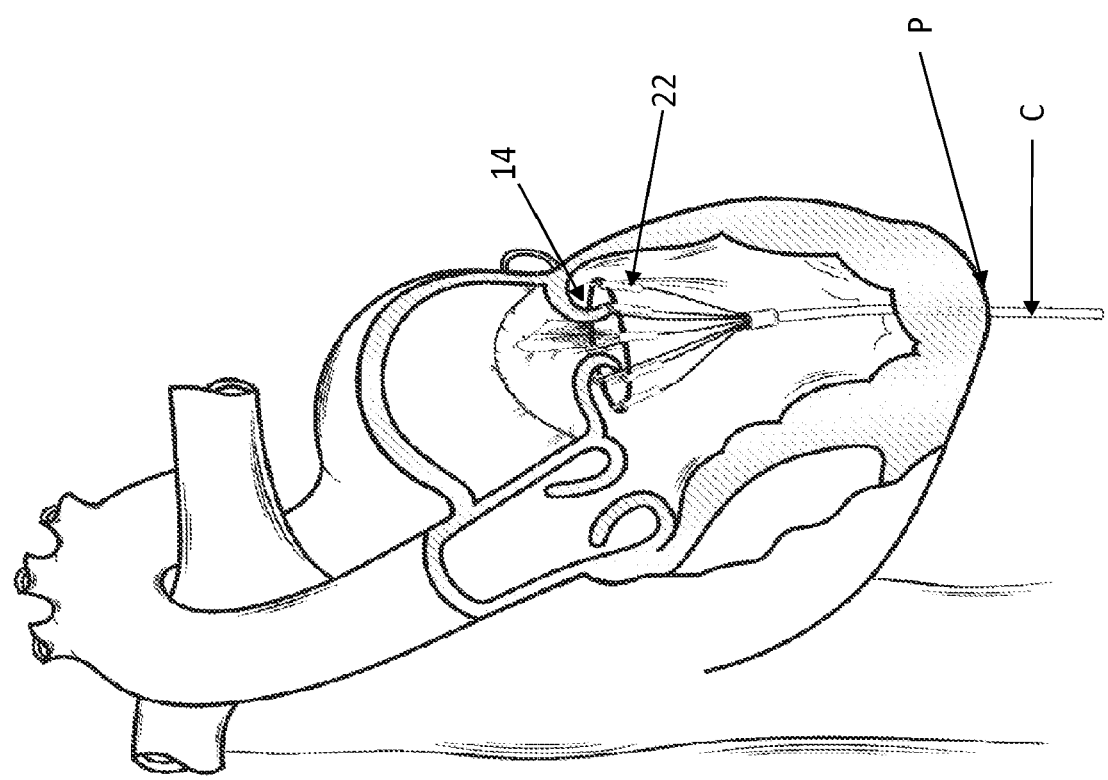
FIGS. 20-22 are front partially cut-away views of a heart with the implant affixed to a mitral valve from below the valve.
Figure 21:
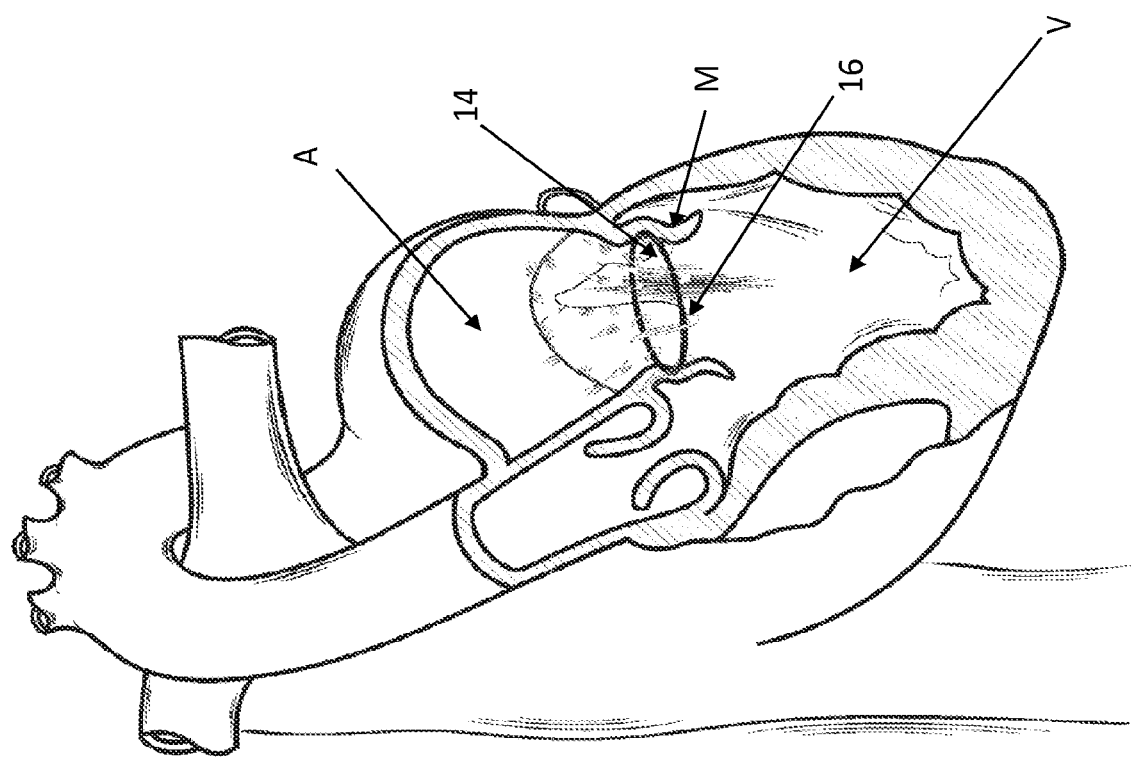
Figure 22:
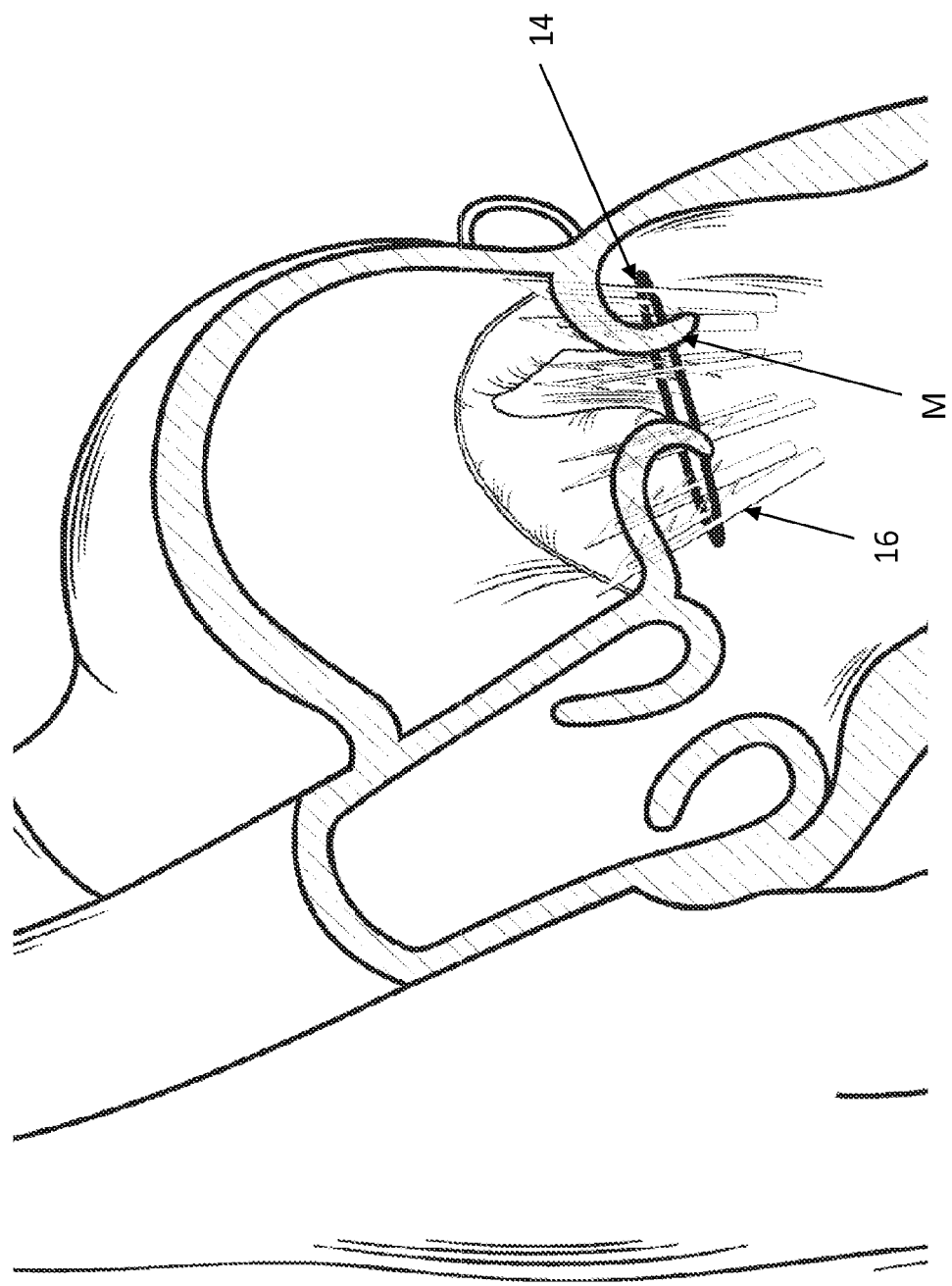

FIGS. 20-24 illustrate embodiments adapted for situations where launching anchors 16 upwardly may also be used in cases where access to the insufficient valve is from below, for example via the Apex (see FIG. 20), is preferable rather than from above. FIGS. 20 and 22 show loop 14 disposed under the Mitral valve leaflets and FIG. 21 shows loop 14 disposed onto the Mitral valve leaflets M as the anchors 16 penetrates through the leaflets pointing from the ventricle side to the atrium side.

Figure 23:
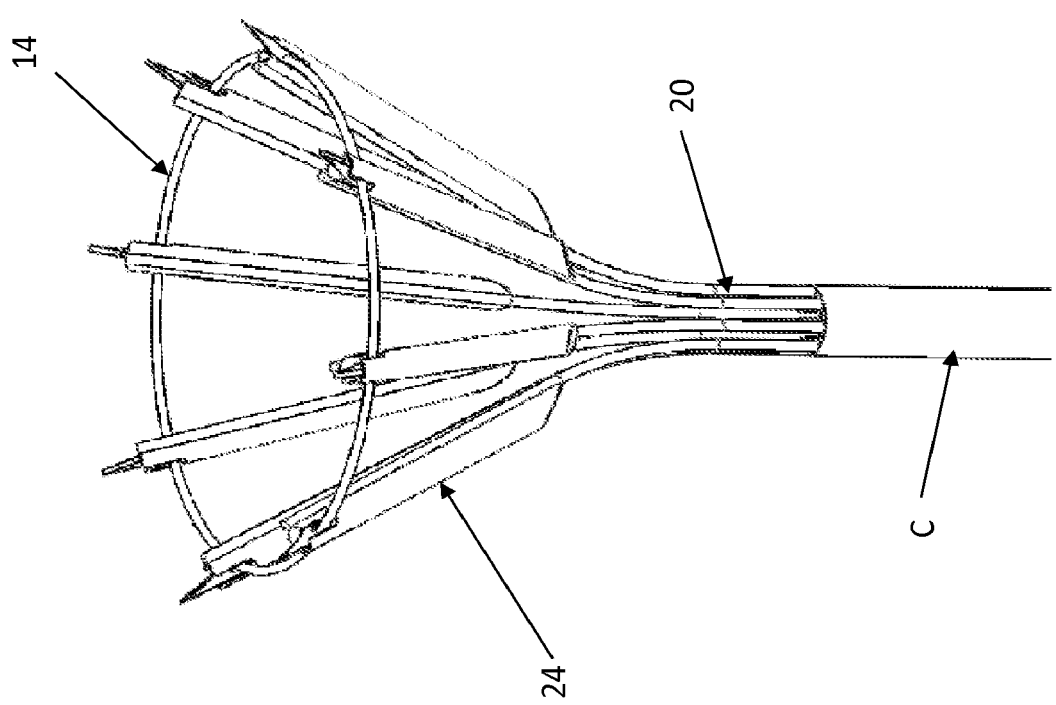
Figure 24:
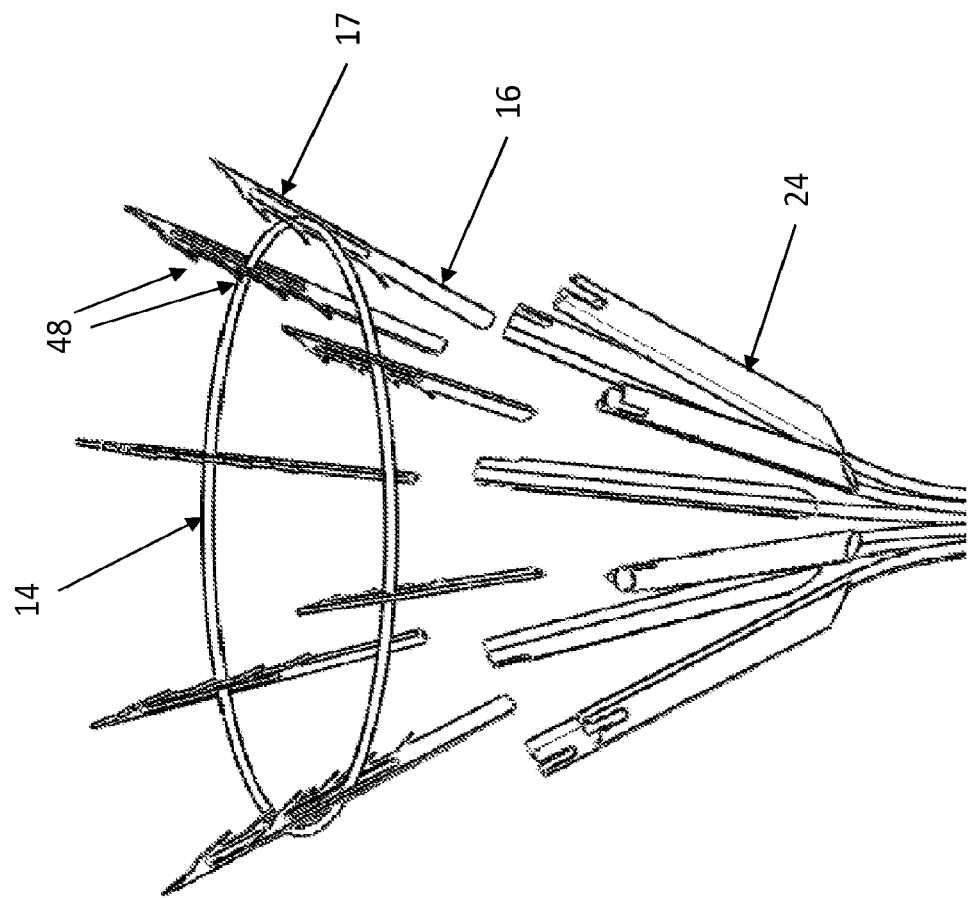

FIGS. 23 and 24 show the pre-launch and launch situations for upward launching of anchors 16. FIG. 23 further illustrates that catheter C can be used to help orient the angle of housings 24, and thus the launch angle of anchors 16. If the distance between catheter C and loop 14 is relatively small, anchors 16 tends to be positioned and launched at a greater angle (relative to being launched perpendicular to loop 14, as was shown in FIGS. 2 and 3, for example). Adjustment of the launch angle, i.e. pivoting of anchors angle, is made possible by the shape of the support arms 20 to which the housing 24 is attached. FIG. 24 also illustrates another modification wherein anchors 16 comprise multiple barbs 48 and wherein elongated slot 17 extends about half-way within the length of the anchors.

Figure 26:
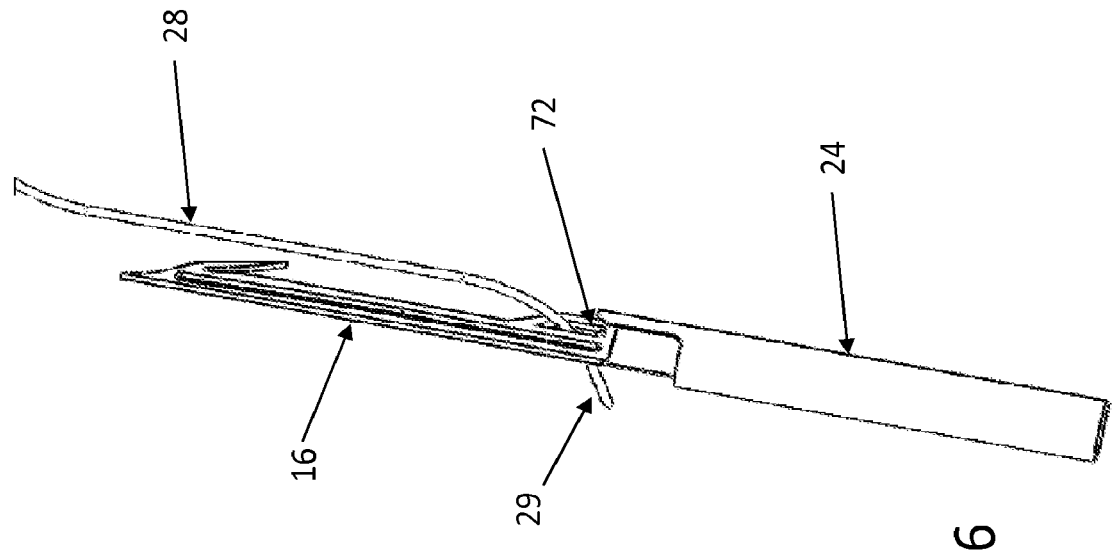
Figure 25:
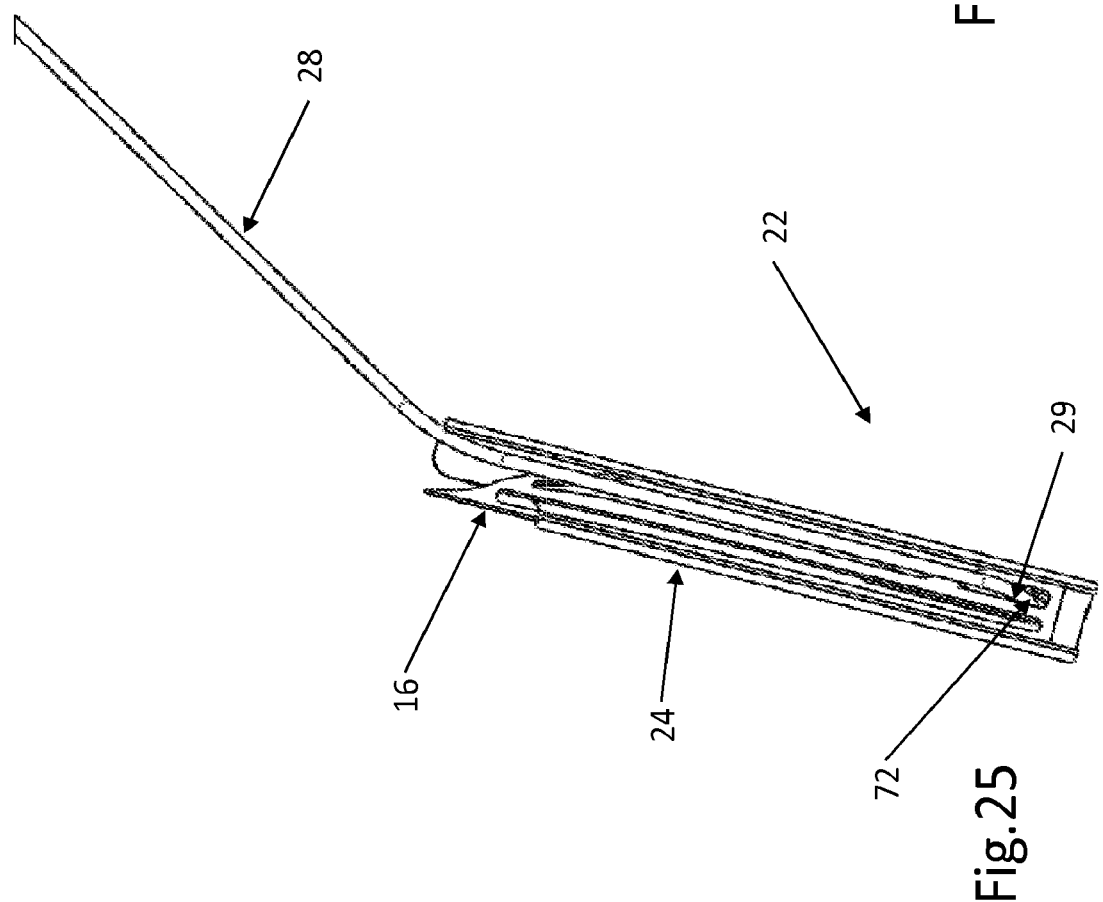

FIGS. 25-27 and 27a illustrate particular embodiments wherein anchor launching mechanism 22 is adapted to be used with tissue anchors 16 that are launched in a generally upward direction; and can be actuated by a direct pull, or by a mechanism removed from the valve area. Anchor launching mechanism 22 comprises actuation wire 28 and housing 24, however the mechanism does not include spring 26 disposed in the housing. Regardless, for rapid actuation purposes (anchor launch), anchor launch mechanism 22 may further include an external launch actuator device, typically including a spring (not shown), for example, at the proximal end of catheter C, to pull on actuation wire 28. When the catheter approaches from the inflow side of the valve, and routes the anchors so that they are below the valve with the tip directed from the ventricle side to the atrium side, this configuration and approach to the valve permits pull wires to be used. [0110] For the purposes of these embodiments, anchor 16 may be modified to further comprise an actuation wire eyelet 72 where-through actuation wire 28. Distal end 29 of actuation wire 28 is threaded through eyelet 72 and typically has a hook-like configuration while disposed within housing 24 (FIGS. 25 and 27). Pulling on actuator wire 28 proximal end to pull (launch) anchor 16 as a result of pulling at eyelet 72 (FIG. 26). In such embodiments, housing 24 need not include a window such as window 30, nor does not need a crimped portion 36 or other such spring retention mechanism, as there is no spring in the housing. FIGS. 27 and 27a illustrates a modification wherein instead of eyelet 72; each anchor 16 has a actuator-wire distal-end receiving portion such as recess 74, which operates to launch anchors 16 in the same fashion as noted above.

Figure 29:
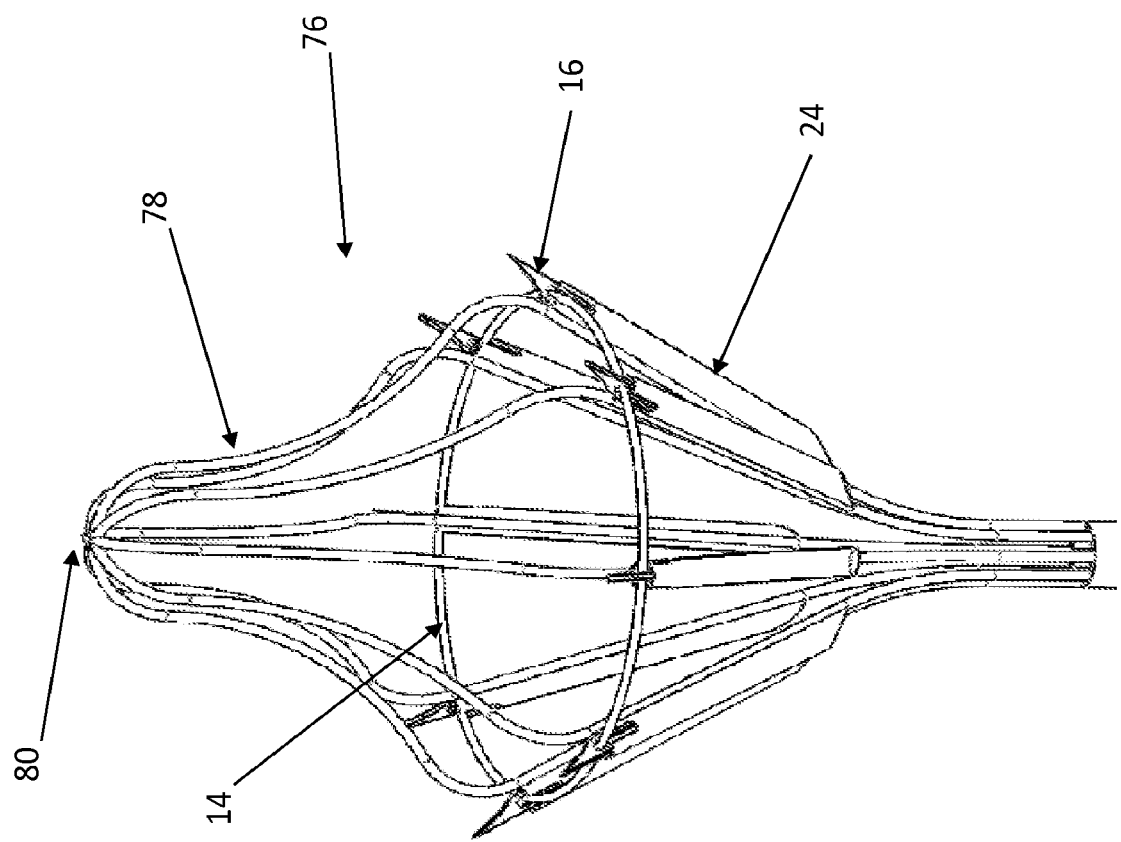
Figure 30:
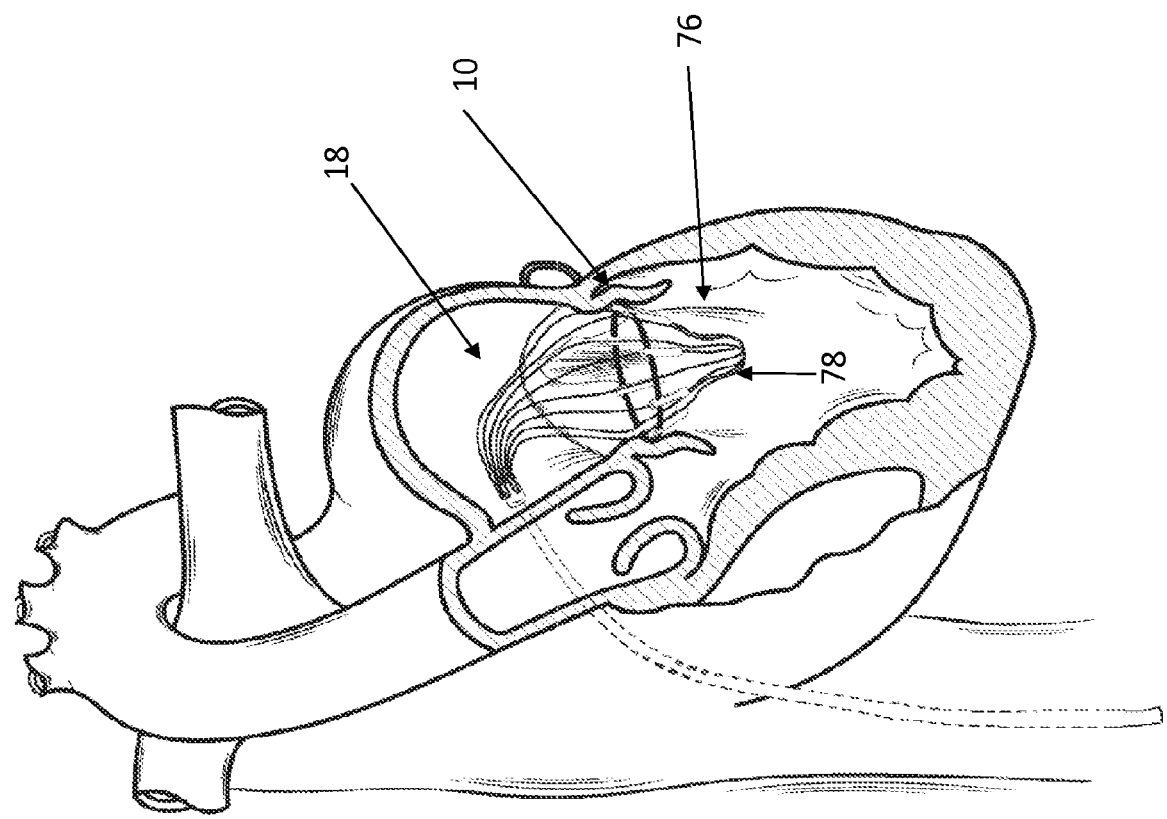

FIGS. 28-30 show embodiments, wherein implant 10 further comprises a loop-arrangement/anchor-orientation mechanism 76 useful for arranging the position and/or shape of loop 14 and/or for orienting the angle of housings 24, and thereby orienting the launch angle of tissue anchors 16. Anchor orientation mechanism 76 includes a plurality of curved arrangement leads 78 respectively attached to at least some of housings 24, for example by welding. Leads 78 may be an extension of implant support arms 20 and may be arranged to cross at a singular intersection point 80. Leads 78 are attached (e.g. by welding) to housing 24. Thus, leads 78 of orientate mechanism 76 are movable to arrange loop 14 in a desired location and depending on the shape of the leads, the angle of housings 24, and thus anchors 16, can be determined.

Regarding the launch angle of anchors 16, in some embodiments, leads 78 can be attached "ad hoc" prior to insertion into a patient, whereby, depending on the attachment location, arrangement leads 78 also be used to orient anchors 16 i.e. control the angle at which the anchors enter the tissue (i.e. changing the length or shape of one or more leads 78 will thus change the angle of the anchors, e.g. shortening the that length will cause the anchors to point outward, whereas increasing that length will bring intersection point 80 farther from loop 14 and thus angle the anchors more parallel to each other (less outward). In such case, leads 78 will not be welded to housings 24, rather there will be included an "ad hoc" connection or fastening arrangement (not shown), whereby the leads and housings are connected at more than one location along the leads. Arrangement/orientation mechanism 76 can be useful for arranging the shape of loop 14 as well as positioning the loop and orienting the anchor angle. In alternative embodiments, loop-arrangement/anchor-orientation mechanism 76 either has a predetermined shape, such as a nipple shape (FIGS. 29 and 30) or is adapted to allow its shape to be changed; i.e. leads 78 can be bent.

Figure 31:
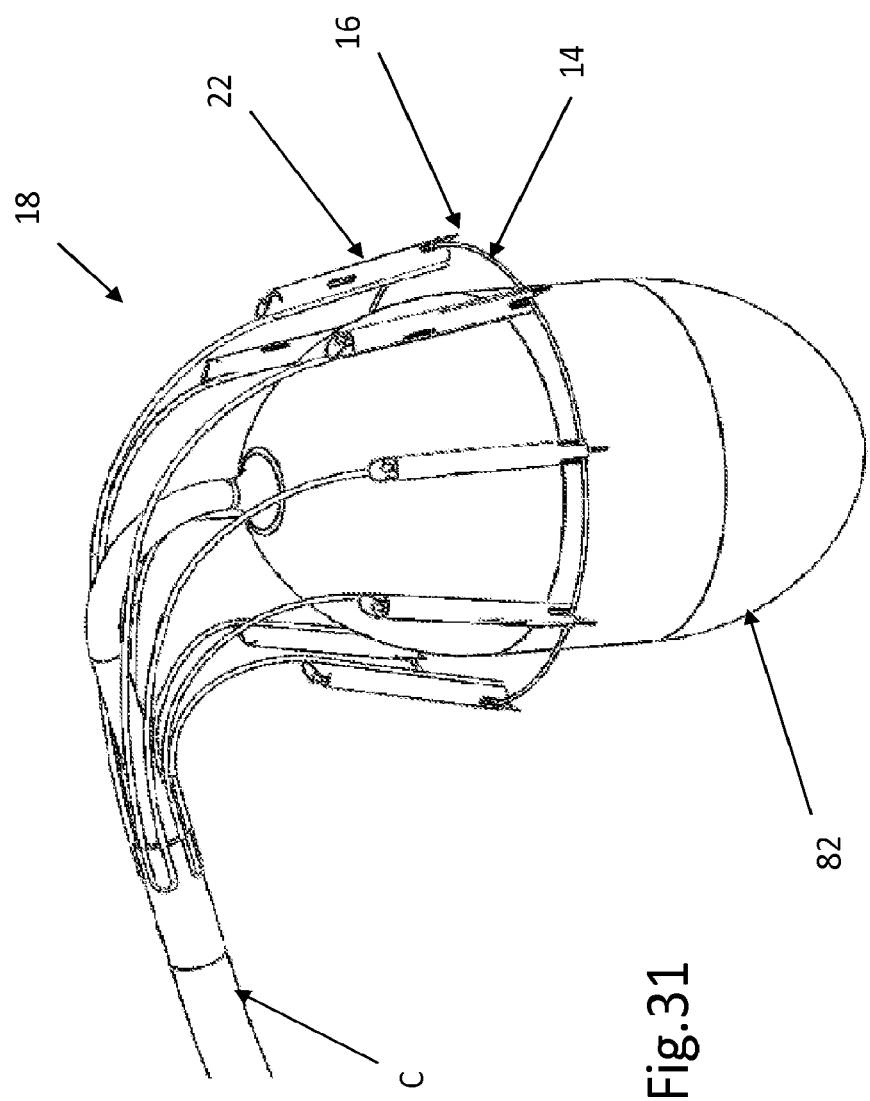
FIGS. 31-34 show embodiments in which loop arrangement and/or implant positioning is implemented using an inflatable balloon.
Figure 32:
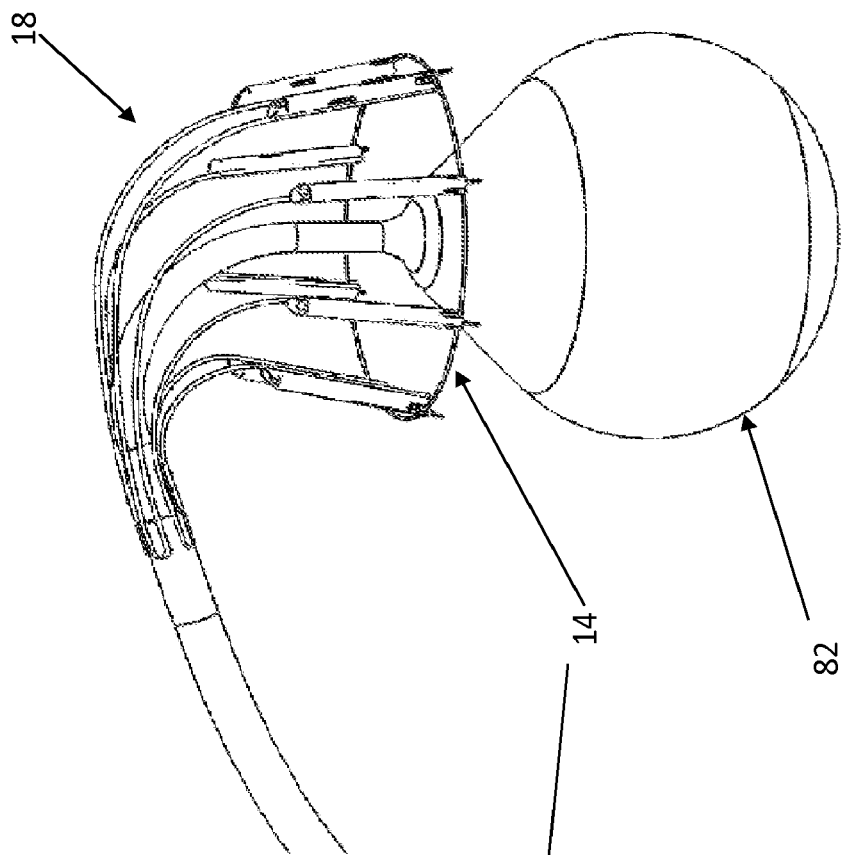
Figure 33:
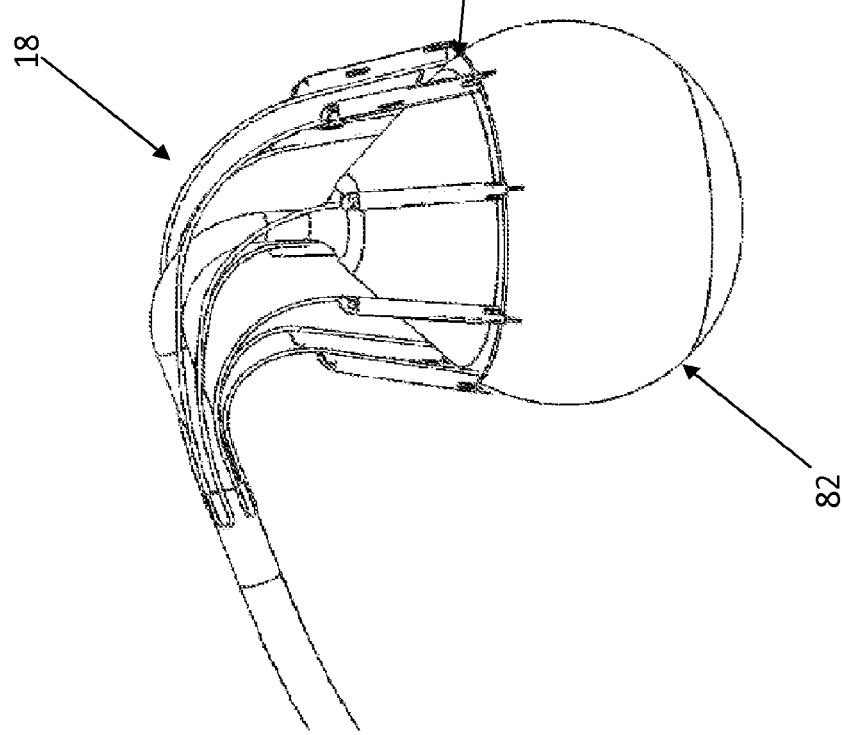
Figure 34:
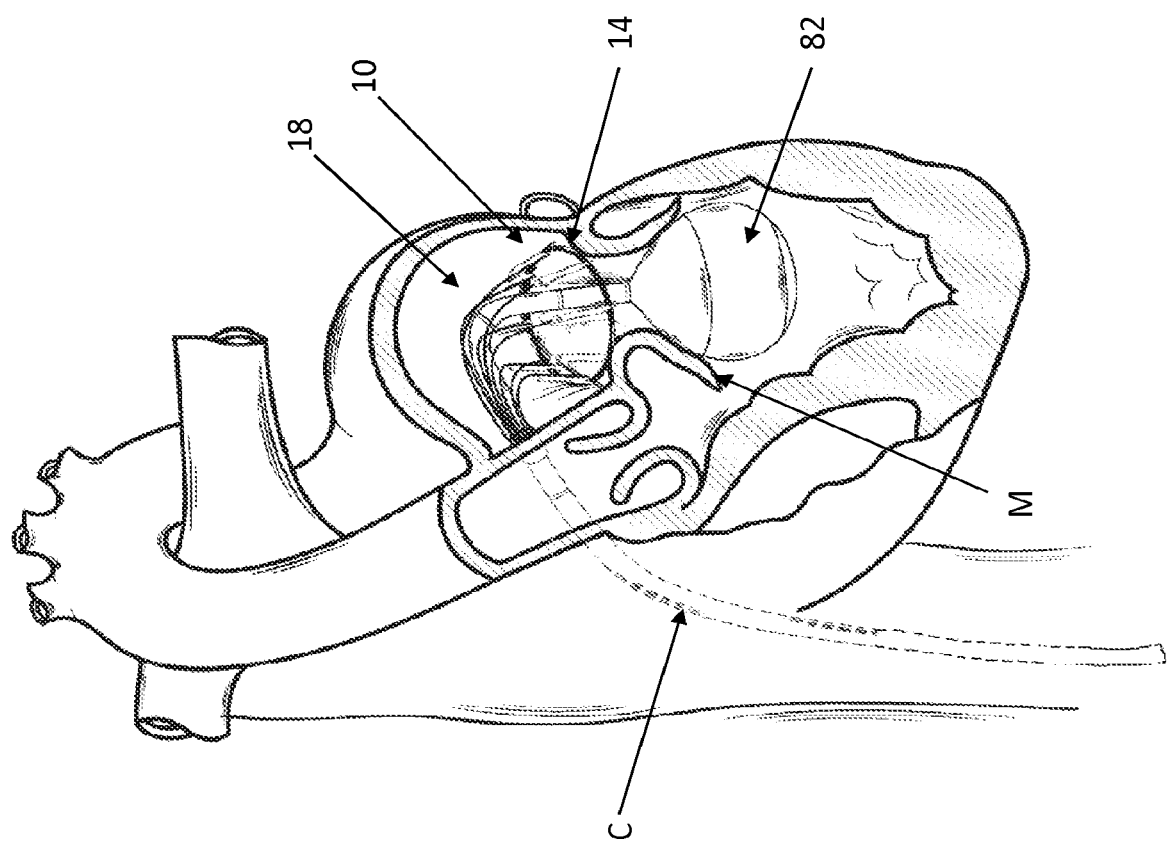

FIGS. 31-34 show embodiments wherein loop arrangement and/or implant positioning device 18 comprises an inflatable balloon 82. The figures show exemplary balloons 82 useful for a) making sure support arms 20 are fully expanded before deploying implant 10, b) make sure that loop 14 is concentric with the valve annulus prior to implantation, and c) facilitating an interference step or backing against which to press to be used for pressing implant positioning device 18 and implant 10 onto the valve annulus before implantation as illustrated in FIG. 34. FIG. 31 illustrates an oval balloon 82; FIGS. 32-34 illustrate a droplet-shaped or bulbous balloon 82.

As seen in FIG. 34, as well as being useful to orient loop 14 relative to the valve annulus, the balloon can be used to secure the implant positioning device 18 and implant 10 in place during launching of anchors 16. FIGS. 32 and 33 also illustrate that balloon 82 can be positioned proximally or distally with respect to loop 14 and implant positioning device 18. Since the balloon can be positioned inside the ventricle and be inflated to a diameter bigger than the diameter of biological valve annulus, it can serve as a backing against which to press positioning device 18 and implant 10 onto the valve annulus before implantation. This will ensure good contact between each of the anchor launching mechanisms 22 and the valve annulus and will create optimal penetration conditions of anchor 16 into the tissue upon launching. Furthermore, the launch angle of anchors 16 (i.e. insertion into the tissue) can be controlled by inflating/deflating balloon 82, with consideration to the size of the biological valve.

Figure 35:
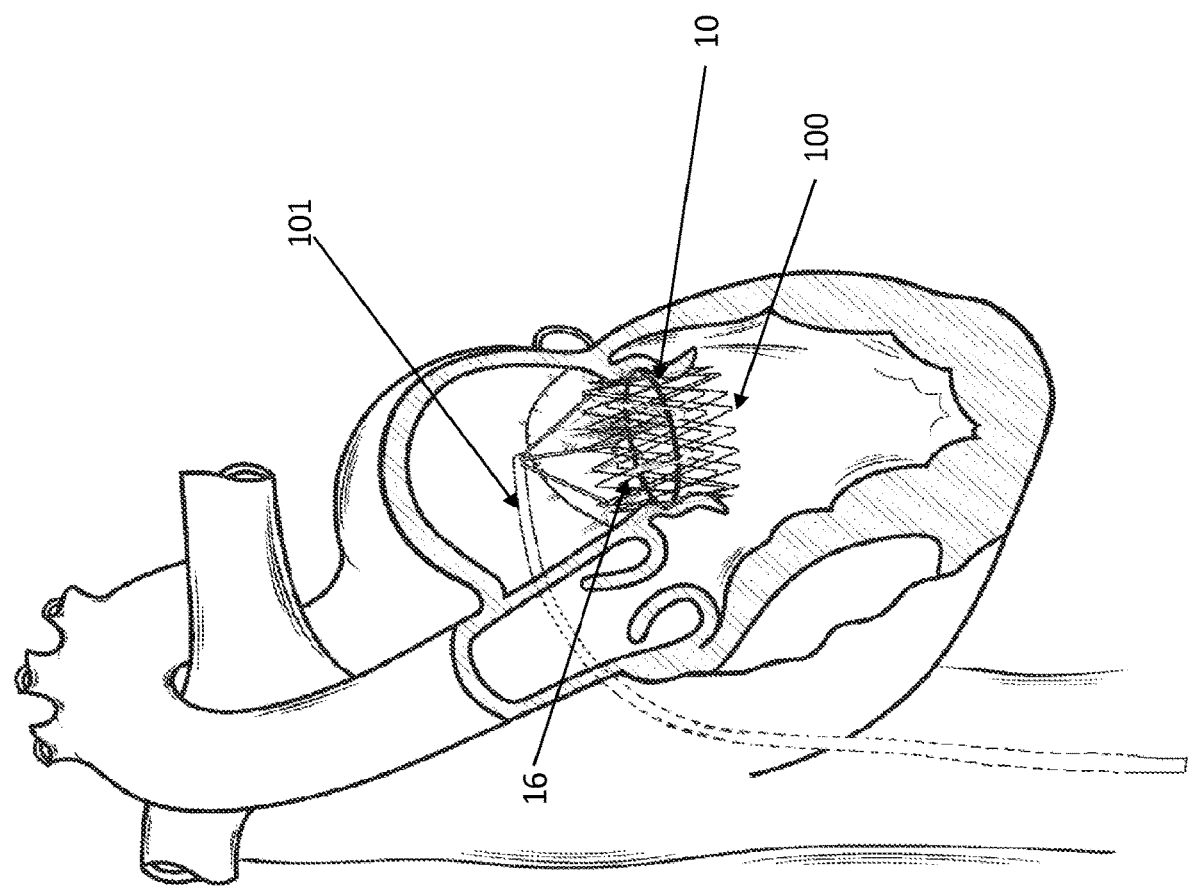
Figure 37:
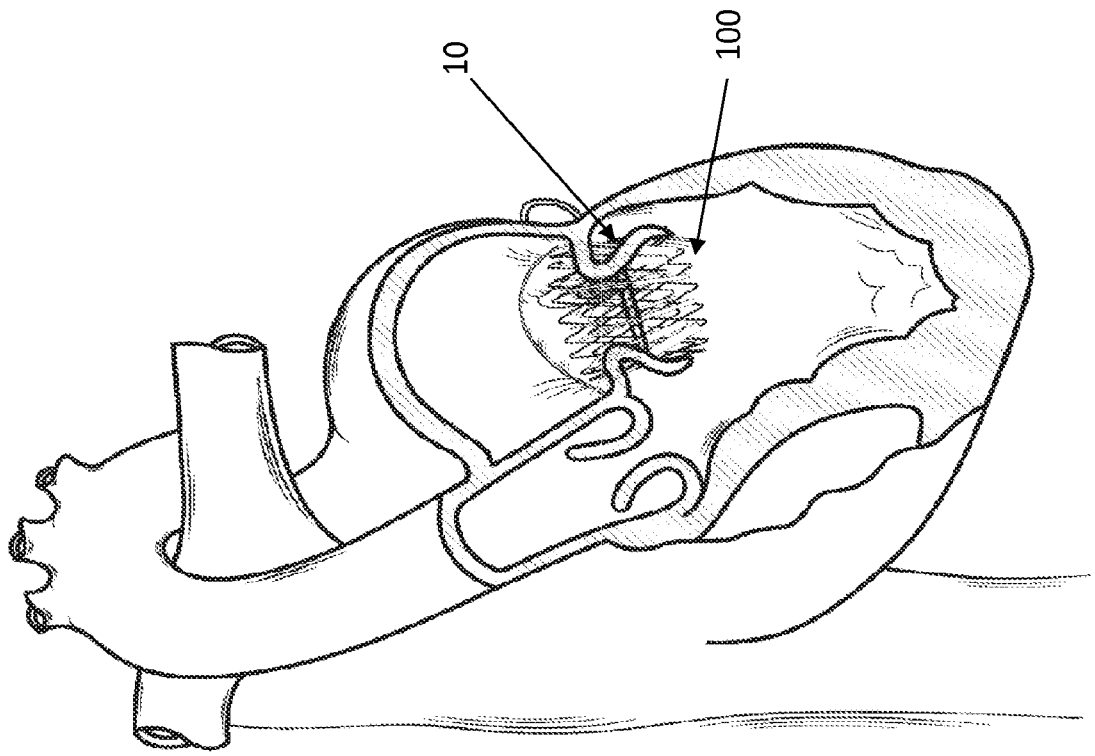
Figure 36:
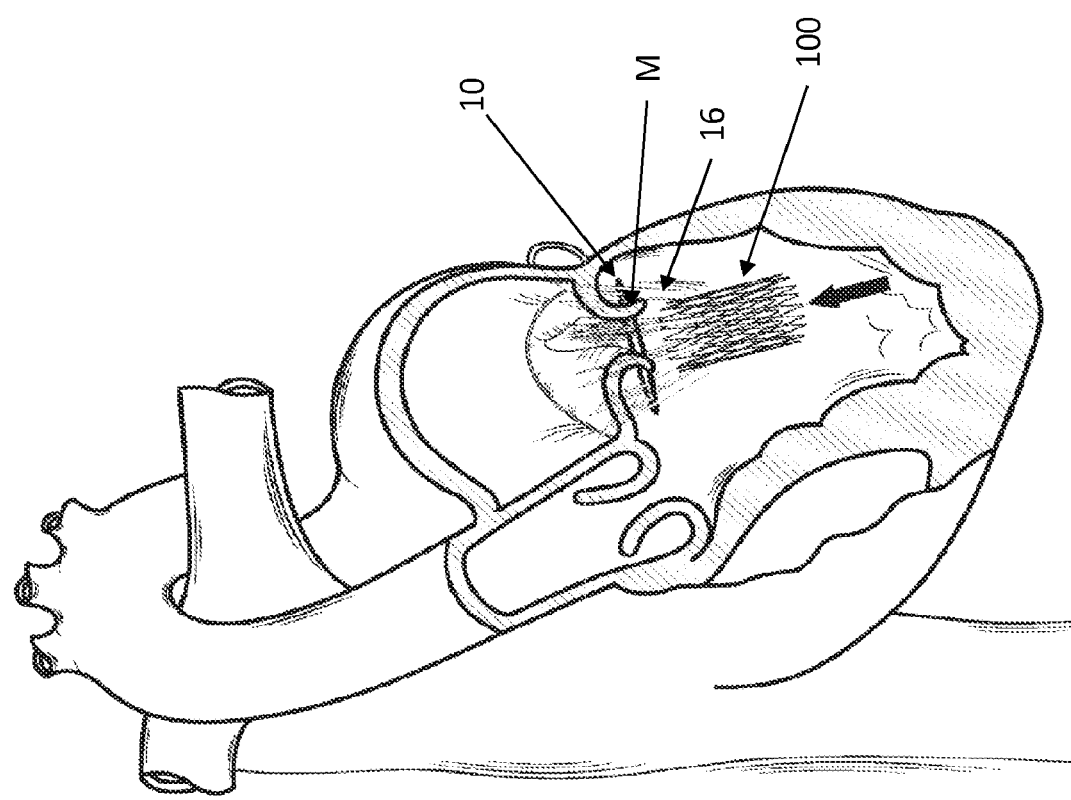

FIGS. 35-37 illustrate how a device 100 (e.g., a replacement valve) can be fixed to a native valve annulus or leaflets like the mitral valve M or tricuspid valve. In this embodiment, implant 10 is first implanted and secured with anchors 16 that penetrate the valve leaflets pointing from the ventricle V side toward the atrium A side (hereinafter upwards) as in FIG. 21 and/or FIG. 22. Then, when device 100 is expanded into implant 10, the friction between anchors 16 and the device 100 secures device 100 in place. Since anchors 16 are directed generally upward, the high pressure in ventricle V helps to further enhance the anchoring of implant 10 to the valve leaflets.

Device 100 in the illustrating figures represents any suitable commercial expandable heart valve prosthesis that can be tracked in a collapsed configuration through the vascular system and delivered to the heart. It can be a self expanding prosthesis or a balloon expanding prosthesis or any other type of expanding heart valve prosthesis. FIG. 35 further illustrates an exemplary delivery system 101 that can deliver device 100 to the heart.

FIGS. 36 and 37 illustrate how implant 10 can be associated with device 100 for fixing the device to a mitral valve M (or tricuspid valve) leaflets. In this embodiment, implant 10 and device 100 are implanted via the heart's apex P, preferably, in a minimally invasive surgery as illustrated in FIG. 20. As in FIG. 22, implant 10 is first located at the proper location with respect to the bio-valve (mitral in this case) and then secured with anchors 16 facing upward, in accordance with any appropriate embodiment as described herein. After implant 10 is attached to the valve leaflets, device 100 is advanced, as shown in FIG. 36. through a delivery catheter (not shown), and expanded into implant 10 as seen in FIG. 37. Since anchors 16 are directed generally upward, the high pressure in the ventricle V helps to further enhance the anchoring of the implant 10 and device 100 to the valve leaflets. However, for the purpose of this embodiment, wherein implant 10 is configured to be particularly suited to securing a device in place such as device 100, each anchor 16 has a relatively shorter slot 17, typically extending only about half-way along the longitudinal dimension of each anchor, from about halfway along the anchor to relatively close to the anchors' pointy front end 46.

With reference to FIGS. 38 and 39, when device 100 is disposed in the appropriate heart (or other biological) valve and expanded, the contact and sliding motion between the device and anchor 16 changes the angle of the anchors from typically approximately 45 degrees (FIG. 38), although, depending on the angle of support arms 20, to an angle wherein the anchors are more parallel to each other, typically substantially parallel. The movement of anchors 16 is illustrated by arc A-B in FIG. 38. In other words, anchors 16 pivots at the end of slot 17, as in FIG. 7a which is generally at mid-point 84 of the anchors. This angle change provides increased friction between anchors 16 and device 100 thereby securing the device in place.

To further explain, device 100 is expanded in the bio-valve until the device presses on a non-slotted portion 86 of anchors 16. As a result of pressing on non-slotted portion 86, that portion is forced outward, and thus the tip of the anchors 46 is moved inward, as the anchors pivot around loop 14. Since anchor tips 46 are locked within the tissue of the valve leaflet, the inward motion of the tips pulls the leaflets closer to device 100 and presses the leaflets against the device, thereby enhancing the sealing and prevent blood flow between the native valve leaflet and the device. It should be understood that device 100 is appropriately sized for the above-described positioning.

Figure 40:
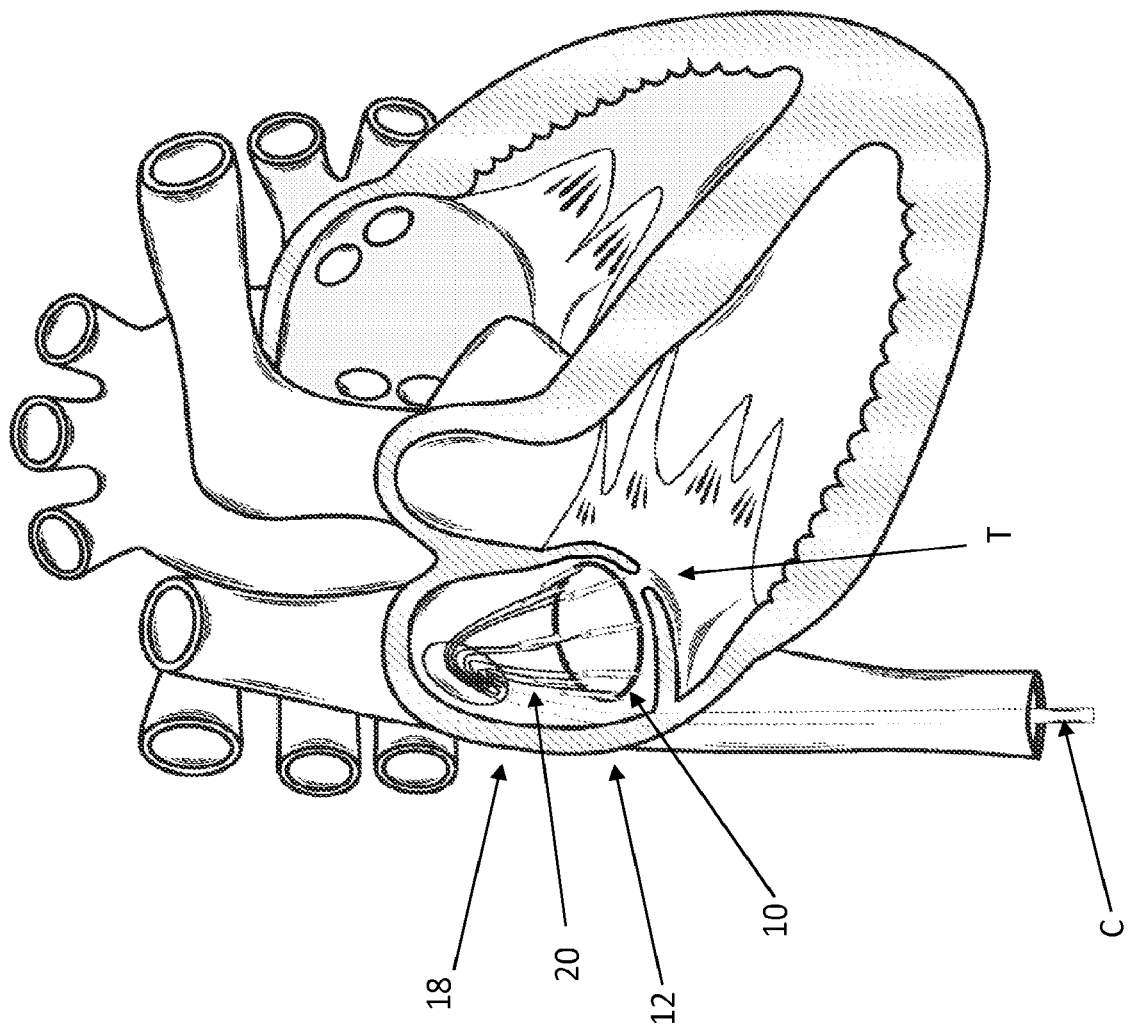
FIG. 40 is a perspective partially cut-away view of the heart with the implant deployed for use on a tricuspid valve.

FIG. 40 illustrates deployment of implant 10 in the tricuspid heart valve T and it should be understood that all the features and functions of the implant and delivery system as illustrated in FIGS. 1 to 39 are applicable to the tricuspid valve.

Figure 41:
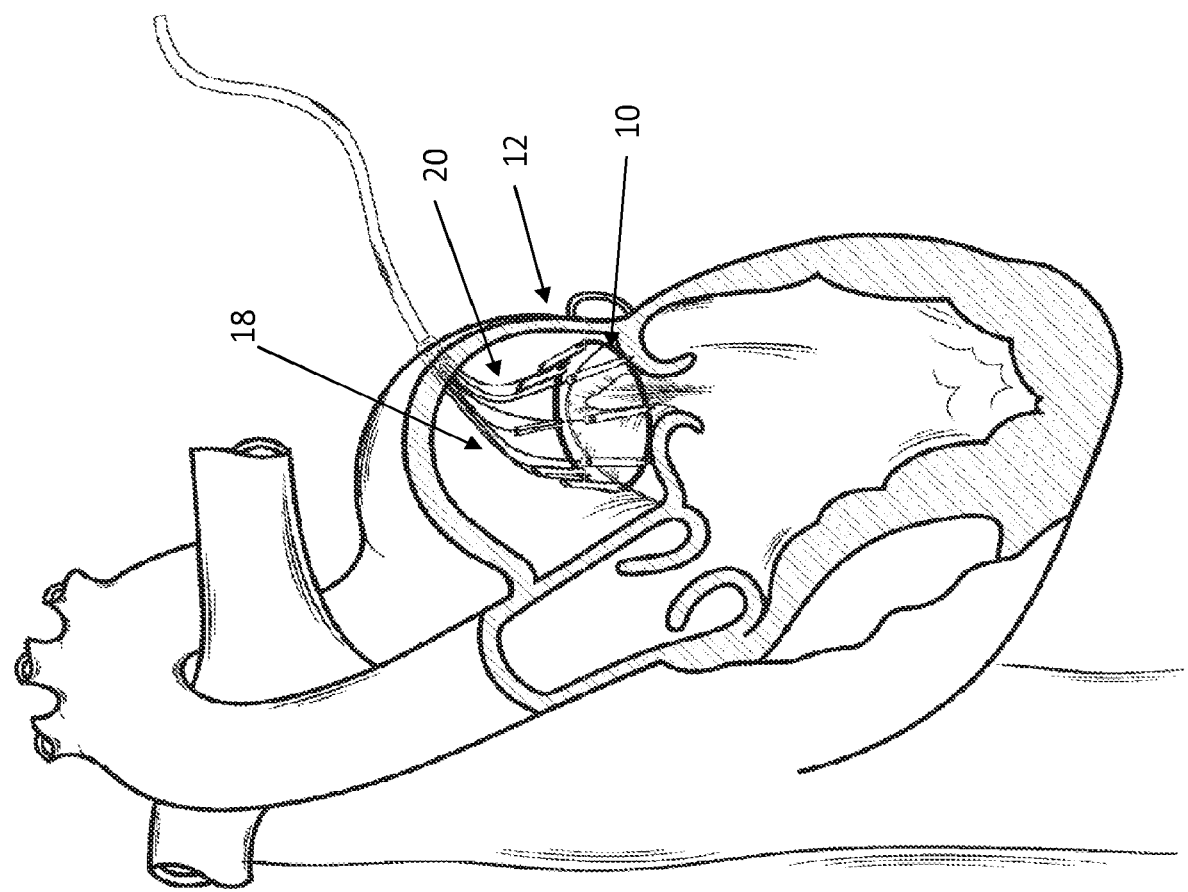
FIG. 41 is a perspective partially cut-away view of the heart with the implant deployed via the left atrium wall.

FIG. 41 illustrates deployment of implant 10 through the left atrium wall rather than tracking in through the vascular system, or deploying the implant through the apex of the heart. Again, it should be understood that all the features and functions of the implant and delivery system illustrated in FIGS. 1 to 39 are applicable to deployment through the atrium wall.

Figure 42:
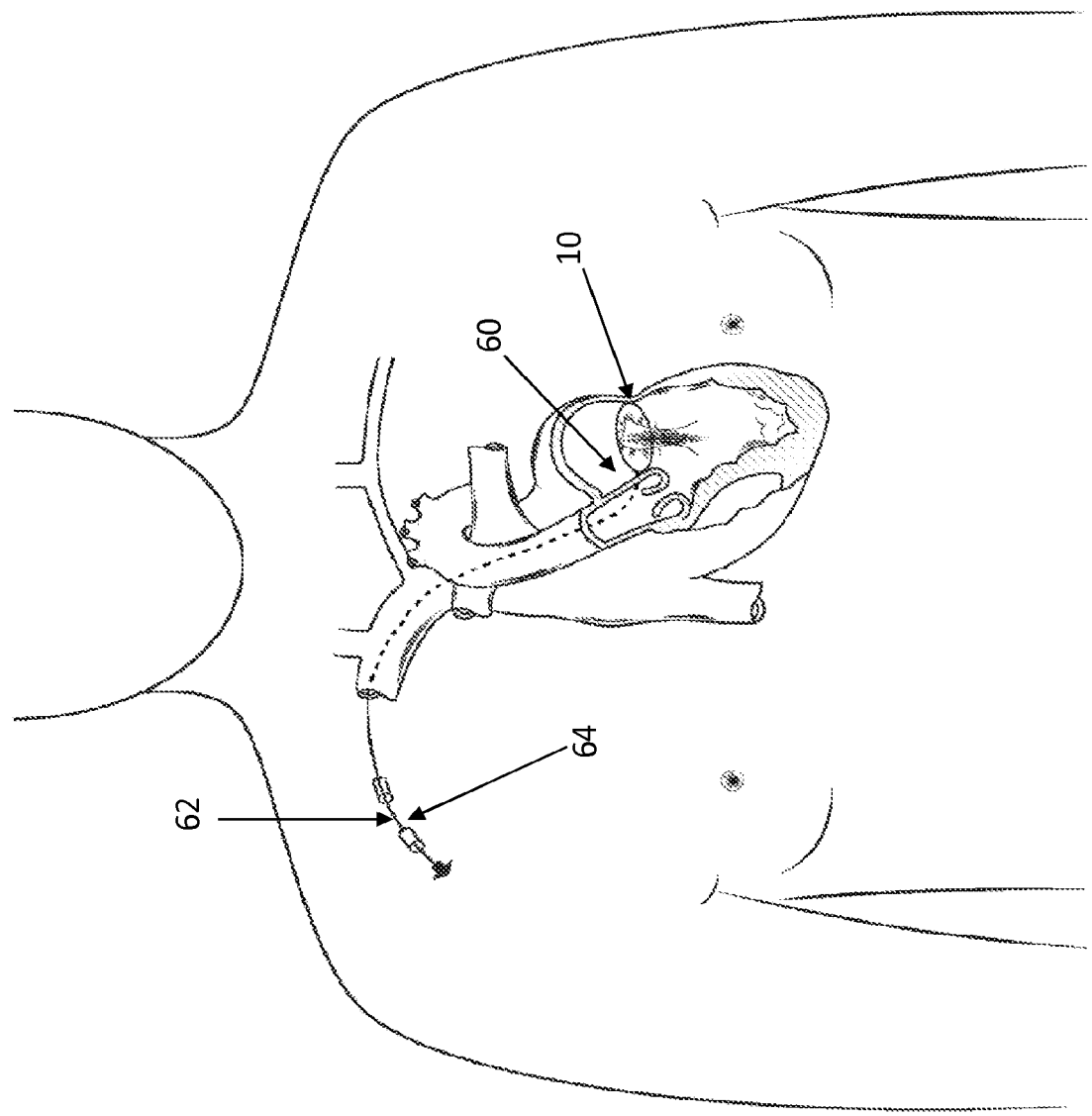
FIG. 42 is a view illustrating manual cinching of the device after tissue healing.

FIG. 42 illustrates manual cinching of the device in a later procedure after tissue healing has occurred as described above with reference to FIG. 14.

Figure 43:
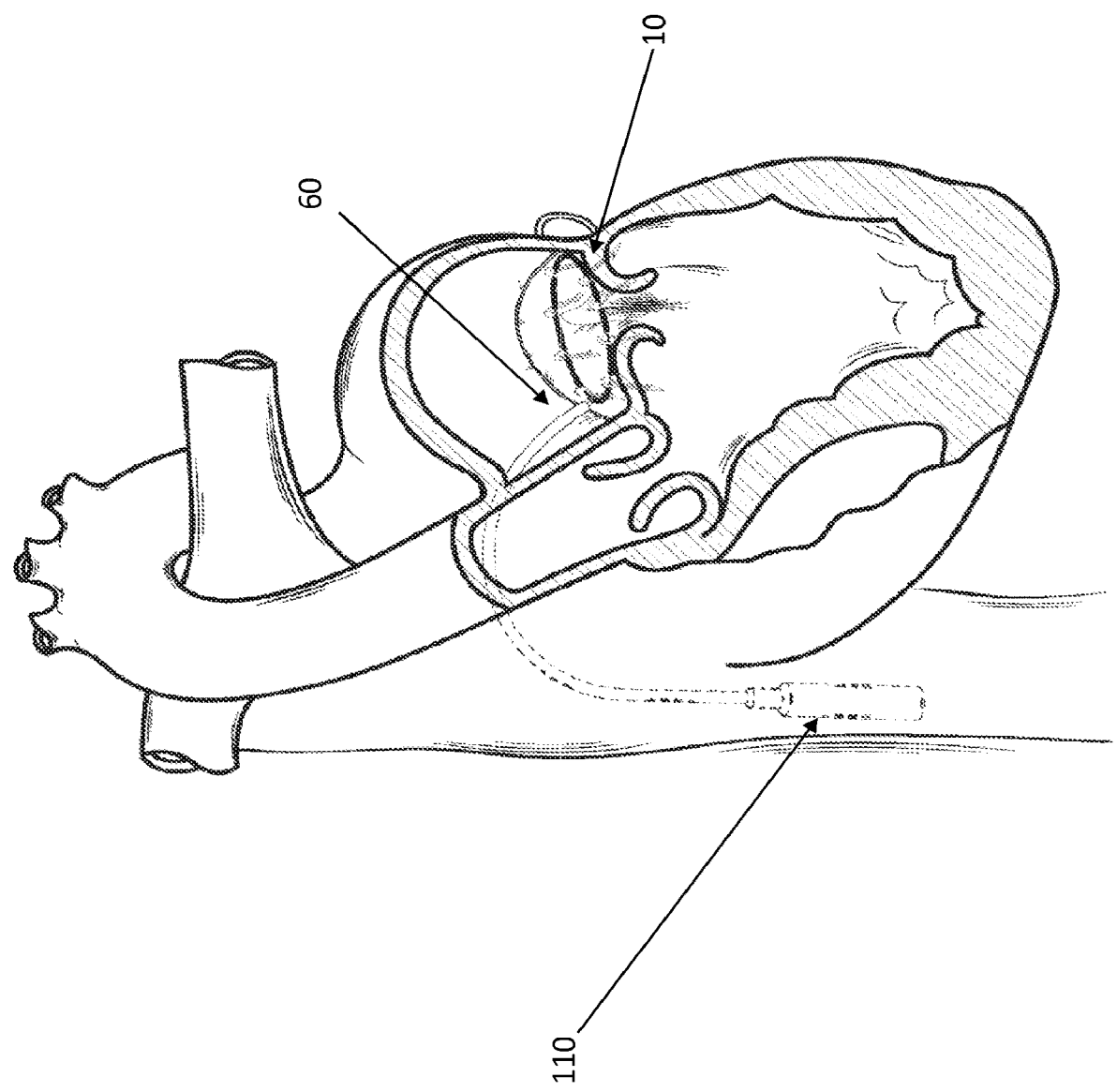
FIG. 43 is a perspective partially cut-away view of the heart illustrating mechanical cinching of the device after tissue healing.

FIG. 43 illustrates cinching of the device in a later procedure after tissue healing has occurred as described above with reference to FIG. 14. Using a mechanical actuator 110 that is implanted during procedure. The mechanical actuator can be actuated and operated magnetically, electrically or by any other appropriate mechanism from outside of the body.

It should be understood that the above description is merely exemplary and that there are various embodiments of the present invention that may be devised, mutatis mutandis, and that the features described in the above-described embodiments, and those not described herein, may be used separately or in any suitable combination; and the invention can be devised in accordance with embodiments not necessarily described above.

What is claimed is:

1. An apparatus configured to rely on leaflets of a native cardiac valve located between a ventricle and an atrium to hold a prosthetic valve at an operative position between the ventricle and the atrium, the leaflets having a ventricle side and an atrium side, the apparatus comprising:
   a closed loop of material;
   a scaffold configured to move between a collapsed state and an expanded state, wherein the scaffold is configured so that in the expanded state, the scaffold is shaped to hold the loop of material at a first position within the ventricle at which the entire loop of material is positioned adjacent to the ventricle side of the leaflets;
   a plurality of anchors configured to anchor the loop of material into the leaflets, each of the anchors having a pointed front tip, wherein the plurality of anchors is positioned with respect to the loop of material so that when the loop of material has been delivered to the first position, the pointed front tip of each of the anchors is directed from the ventricle side of the leaflets to the atrium side of the leaflets; and
   a plurality of anchor launchers supported by the scaffold, each of the anchor launchers configured to, after the loop of material has been delivered to the first position, drive a respective one of the plurality of anchors into one of the leaflets in a direction from the ventricle side of the leaflets to the atrium side of the leaflets so that the respective anchor becomes implanted into one of the leaflets,
wherein the loop of material and the plurality of anchors are configured to cooperate to hold the prosthetic valve at the operative position between the ventricle and the atrium upon expansion of the prosthetic valve within the loop of material, and
   wherein each of the anchors includes a slot configured to permit the anchor to slide with respect to the loop of material in a direction that is perpendicular to the loop of material at such time when the anchor launchers drive the anchors into the ventricle side of the leaflets.

2. The apparatus of claim 1, wherein the slot in each of the anchors comprises a linear slot.

3. The apparatus of claim 1, wherein the slot in each of the anchors comprises a linear slot that extends along a longitudinal dimension of the anchor, from about halfway along the anchor towards the pointed front tip of the anchor.

4. The apparatus of claim 1, wherein each of the anchors has a front portion that is slotted and a rear portion that is non-slotted, and wherein the slotted front portion is configured to permit the anchor to slide with respect to the loop of material in a direction that is perpendicular to the loop of material at such time when the anchor launchers drive the anchors into the ventricle side of the leaflets.

5. The apparatus of claim 4, wherein the plurality of anchors is configured with respect to the loop of material so that contact and sliding motion between the prosthetic valve and the plurality of anchors will reorient the plurality of anchors from an initial orientation to a second orientation at which the anchors are more parallel to each other than in the initial orientation.

6. The apparatus of claim 5, wherein in the second orientation, the anchors are substantially parallel to each other.

7. The apparatus of claim 1, wherein each of the anchors has a slotted front portion and a non-slotted rear portion, and wherein the plurality of anchors is configured with respect to the loop of material so that (a) expanding the prosthetic valve within the loop of material will push the rear portions of the plurality of anchors outward, and (b) outward motion of the rear portions of the plurality of anchors will cause the plurality of anchors to pivot so that the pointed front tips of the plurality of anchors move inward, thereby pressing the leaflets against the prosthetic valve.

8. The apparatus of claim 1, wherein each of the anchor launchers comprises a linear spring configured so that expansion of the spring will launch a respective anchor into leaflet tissue.

9. The apparatus of claim 8, wherein the scaffold comprises a plurality of support arms, with each of the support arms supporting a respective one of the plurality of anchor launchers.

10. The apparatus of claim 9, wherein each of the anchors has a slotted front portion and a non-slotted rear portion, and wherein the plurality of anchors is configured with respect to the loop of material so that (a) expanding the prosthetic valve within the loop of material will push the rear portions of the plurality of anchors outward, and (b) outward motion of the rear portions of the plurality of anchors will cause the plurality of anchors to pivot so that the pointed front tips of the plurality of anchors move inward, thereby pressing the leaflets against the prosthetic valve.

11. The apparatus of claim 1, further comprising the prosthetic valve, wherein the prosthetic valve is expanded within the loop of material.

12. The apparatus of claim 1, wherein the loop of material is made of metal wire.

13. The apparatus of claim 1, wherein the loop of material is non-elastic.

14. The apparatus of claim 1, wherein the ventricle is a left ventricle, the atrium is a left atrium, and the native cardiac valve is a mitral valve.

15. The apparatus of claim 1, wherein the ventricle is a right ventricle, the atrium is a right atrium, and the native cardiac valve is a tricuspid valve.

* * * * *